(12) United States Patent  (10) Patent No.: US 7,671,888 B2
Nogami et al.  (45) Date of Patent: Mar. 2, 2010

(54) STEREOSCOPIC-ENDOSCOPE DISPLAY CONTROL APPARATUS AND STEREOSCOPIC ENDOSCOPE SYSTEM

(75) Inventors: Shingo Nogami, Machida (JP); Masahiro Kudo, Hino (JP); Takahiro Kogasaka, Hachioji (JP); Kazuo Morita, Hachioji (JP); Kazuo Banju, Hachioji (JP); Masayuki Irie, Hachioji (JP)

(73) Assignee: Olympus Corporation, Tokyo (JP)

( * ) Notice: Subject to any disclaimer, the term of this patent is extended or adjusted under 35 U.S.C. 154(b) by 472 days.

(21) Appl. No.: 11/347,853

(22) Filed: Feb. 6, 2006

(65) Prior Publication Data

US 2006/0126176 A1  Jun. 15, 2006

Related U.S. Application Data

(63) Continuation of application No. PCT/JP2004/011638, filed on Aug. 6, 2004.

(30) Foreign Application Priority Data

Aug. 8, 2003  (JP) .............................. 2003-290852

(51) Int. Cl.
*H04N 13/00* (2006.01)
*A61B 1/04* (2006.01)

(52) U.S. Cl. ....................................................... 348/45
(58) Field of Classification Search ................... 348/45
See application file for complete search history.

(56) References Cited

U.S. PATENT DOCUMENTS 5,416,510 A  5/1995  Lipton et al.
5,577,991 A *  11/1996  Akui et al. .................. 600/111
5,864,359 A  1/1999  Kazakevich
6,324,001 B2 *  11/2001  Tabata ........................ 359/462
6,411,326 B1  6/2002  Tabata
2003/0060679 A1  3/2003  Murata et al.

FOREIGN PATENT DOCUMENTS

| JP | 06-194580 | 7/1994 |
| JP | 6-261860 | 9/1994 |
| JP | 08-065715 | 3/1996 |
| JP | 08-191462 | 7/1996 |
| JP | 08-313825 | 11/1996 |
| JP | 10-221775 | 8/1998 |
| JP | 2000-507402 | 6/2000 |
| JP | 2003-079580 | 3/2003 |
| WO | WO 96/38986 | 12/1996 |
| WO | WO 99/37098 | 7/1999 |

* cited by examiner

*Primary Examiner*—Nhon T Diep
(74) *Attorney, Agent, or Firm*—Scully, Scott, Murphy & Presser, P.C.

(57) ABSTRACT

The present invention provides a system including a stereoscopic endoscope having left and right image pickup units for picking up parallactic images of an object through objective lenses laterally arranged at a distance from each other and CCDs laterally arranged at a distance from each other. In the stereoscopic endoscope, the focal distance is variable by moving focusing lenses. A display control unit is constructed so as to mask image pickup areas in left and right images display in left and right display elements on the basis of information regarding the distance to an object, the image pickup areas being picked up-only by one of the left and right image pickup units. Thus, images corresponding to an area that is picked up in common by both the left and right image pickup units are displayed.

16 Claims, 18 Drawing Sheets

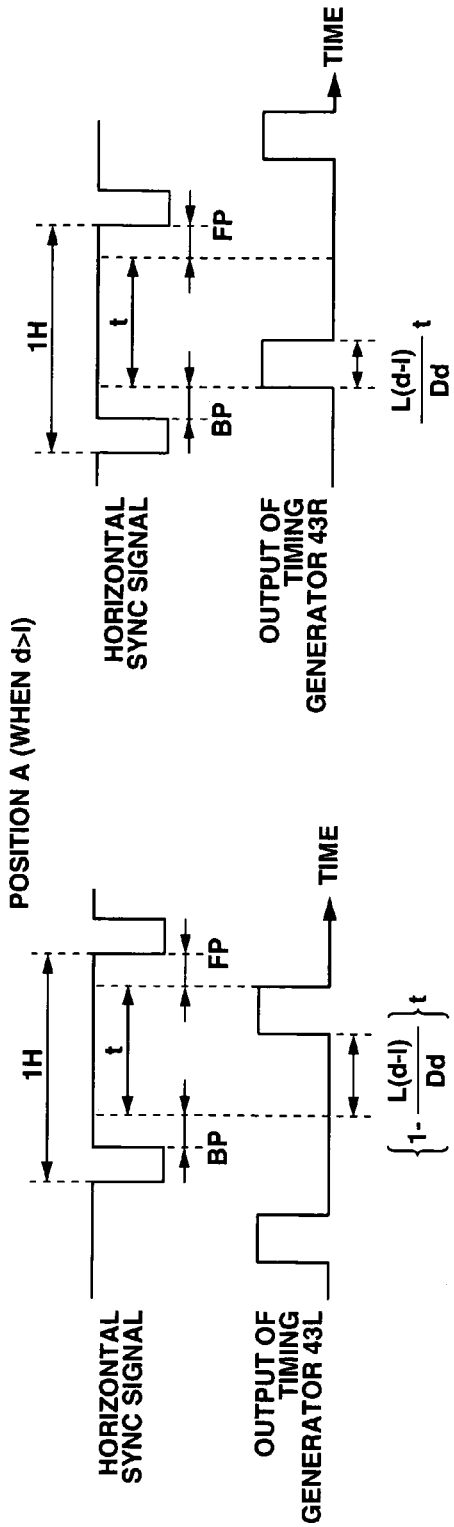
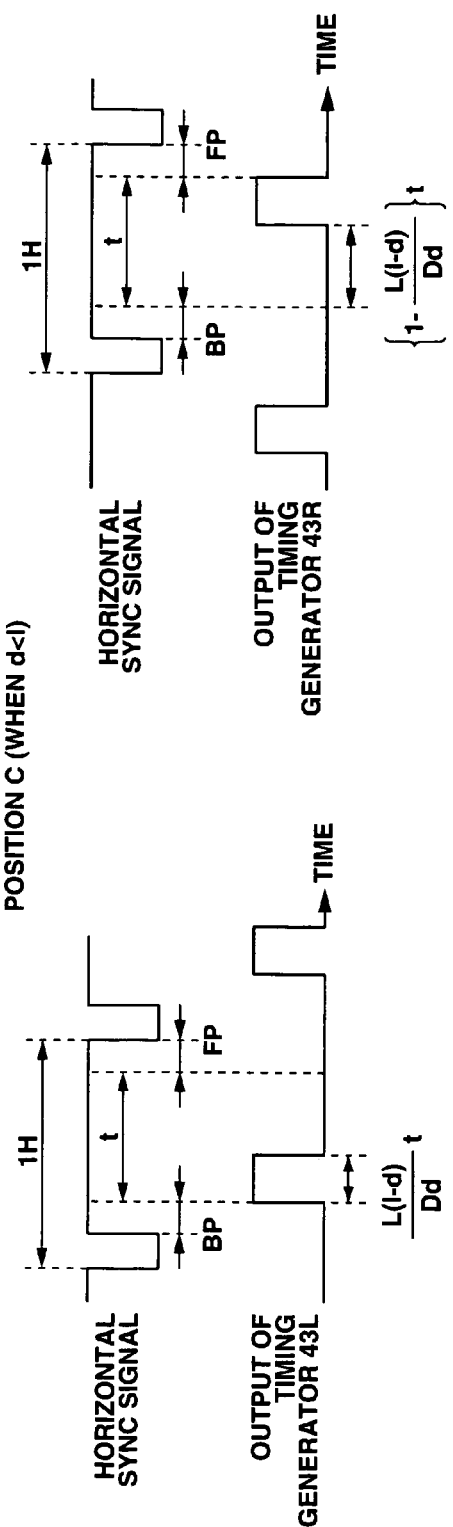

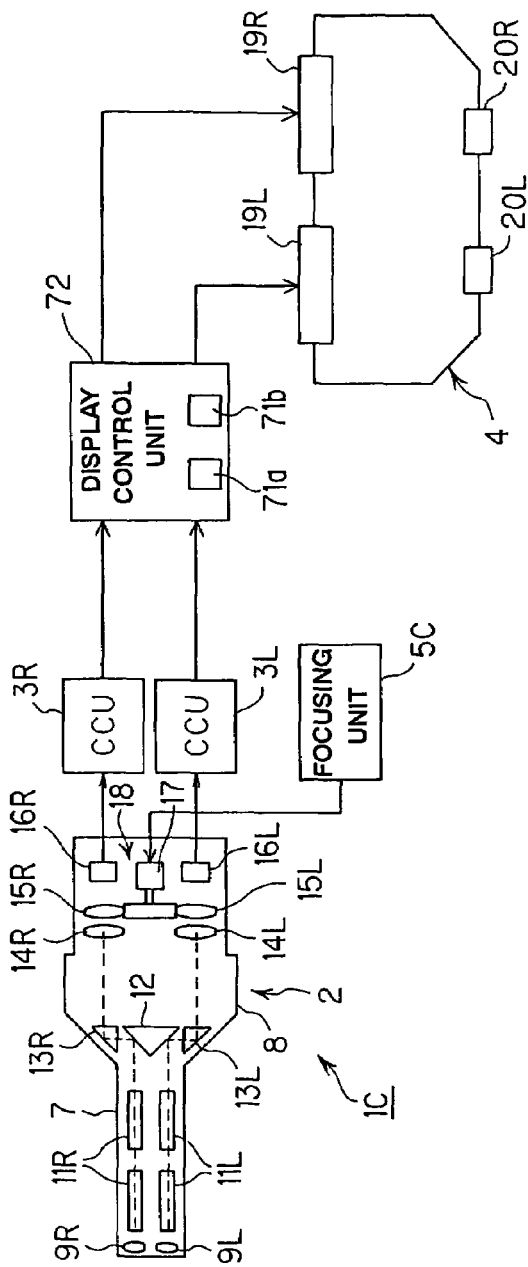
FIG.14
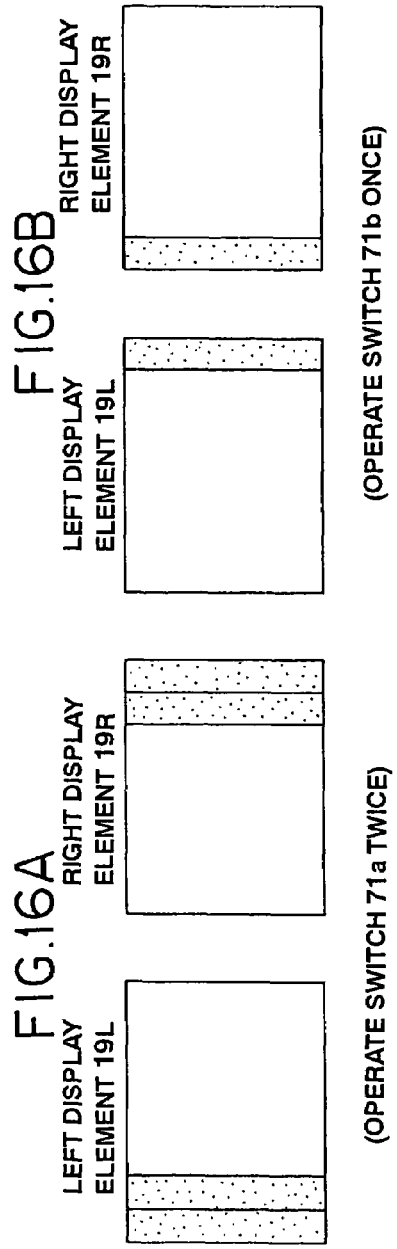
FIG.16A (OPERATE SWITCH 71a TWICE)
FIG.16B (OPERATE SWITCH 71b ONCE)

STEREOSCOPIC-ENDOSCOPE DISPLAY CONTROL APPARATUS AND STEREOSCOPIC ENDOSCOPE SYSTEM

CROSS REFERENCE TO RELATED APPLICATION

This application is a continuation application of PCT/JP2004/011638 filed on Aug. 6, 2004 and claims benefit of Japanese Application No. 2003-290852 filed in Japan on Aug. 8, 2003, the entire contents of which are incorporated herein by this reference.

BACKGROUND OF THE INVENTION

1. Field of the Invention

The present invention relates to a stereoscopic-endoscope display control apparatus and a stereoscopic endoscope system which permit stereoscopic viewing using a stereoscopic endoscope.

2. Description of the Related Art

In general, endoscope systems for endoscopic surgery under observation using an endoscope are widespread.

According to stereoscopic endoscope systems using a stereoscopic endoscope having stereoscopic vision, stereoscopic observation can be performed, thus providing such an environment that surgery can be smoothly performed even when the surgery requires exacting tasks.

A stereoscopic endoscope picks up right and left images having a parallax using right and left optical systems. In this case, the distance between an object and objective lenses where right and left object images match with each other (except the difference therebetween due to a parallax) is in advance designed in the stereoscopic endoscope. If the distance therebetween is shifted from a design point, the display positions of the object displayed in a display element differ therebetween.

The difference between right and left points of view recognized in the brain allows a human being to perceive the depth and dimension of an object in view. Thus, stereoscopic viewing can be ensured. FIG. 18 shows the schematic structure of a conventional stereoscopic endoscope system 90.

The stereoscopic endoscope system 90 includes a stereoscopic endoscope 91, camera control units (hereinbelow, abbreviated to CCUs) 93L and 93R for processing image pickup signals obtained by the CCDs 92L and 92R arranged in the stereoscopic endoscope 91, and display elements 94L and 94R for displaying video signals generated by the CCUs 93L and 93R.

At the distal end of the stereoscopic endoscope 91, objective lenses 95L and 95R are laterally arranged at a distance from each other. Each objective lens receives light from an object located in the front of the lens and forms an image on the corresponding CCD 92L or 92R arranged in the rear of the lens via a group of relay lens (not shown).

The observation distance between an object and the stereoscopic endoscope 91 varies. The stereoscopic endoscope 91 is designed, referring to FIG. 18, when the object is located at a position B, images are respectively formed in the centers of the CCDs 92L and 92R such that the images present the same state (the images match with each other) except the difference therebetween due to a parallax. The images in the same state are displayed in the display elements 94L and 94R, respectively. In other words, actually, there is a parallax, so that the difference caused by the parallax permits stereoscopic viewing (stereopsis).

FIG. 19 shows areas where observation states vary depending on the setting states of the objective lenses 95L and 95R. As shown in FIG. 19, there are an areas that is observed by the objective lens 95R but is not observed by the objective lens 95L and another area which is observed by the objective lens 95L but is not observed by the objective lens 95R.

Accordingly, observed images displayed in the left and right display elements 94L and 94R are as shown in FIGS. 20A to 20C. FIG. 20A shows observed images obtained when the object is located in a position A. FIG. 20B shows observed images obtained when the object is located in the position B. FIG. 20C show observed images obtained when the object is located in a position C.

Referring to FIGS. 20A to 20C, when the object is located in the position A or C such that the distance from the objective lenses is different from the distance between the position B and the objective lenses, there is an area that is displayed in the right display element 94R but is not displayed in the left display element 94L and another area that is displayed in the left display element 94L but is not displayed in the right display element 94R.

Japanese Unexamined Patent Application Publication No. 6-261860 discloses a system including parallax control means arranged in a stereoscopic endoscope in order to solve a feeling of strangeness in stereoscopic viewing.

SUMMARY OF THE INVENTION

The present invention provides a stereoscopic-endoscope display control apparatus that allows a display device to display left and right images corresponding to left and right image pickup signals obtained by picking up images of a single object through left and right image pickup devices that are arranged in a stereoscopic endoscope and have a parallax, the apparatus including:

a masking device for masking image pickup areas in the left and right images displayed by the display device, the image pickup areas being not picked up in common by both the left and right image pickup devices.

BRIEF DESCRIPTION OF THE DRAWINGS

FIGS. 1 to 9 relate to a first embodiment of the present invention, FIG. 1 being a diagram of the entire structure of a stereoscopic endoscope system according to the first embodiment of the present invention.

FIG. 2 is a block diagram of the structure of a focusing unit.

FIG. 3 is a perspective view of a grasping portion of a stereoscopic endoscope, FIG. 3 showing the detailed arrangement of components in the vicinity of a focusing mechanism in the grasping portion.

FIG. 4 is a block diagram of the structure of a display control unit.

FIG. 5 is a flowchart of the process of a computing unit.

FIG. 6 is a diagram explaining observation ranges of left and right objective lenses, the ranges varying depending on the distance to an object.

FIGS. 7A and 7B are timing charts of the masking operations based on outputs of timing generators with respect to positions A and C in FIG. 6, respectively.

FIG. 8 is a block diagram of the structure of a display control unit according to a modification of the first embodiment.

FIG. 9 is a diagram explaining the operation of a memory controller in FIG. 8.

FIGS. 10 to 13C relate to a second embodiment of the present invention, FIG. 10 being a diagram of the entire structure of a stereoscopic endoscope system according the second embodiment of the present invention.

FIG. 11 is a block diagram of the structure of a focusing unit.

FIG. 12 is a diagram of the internal structure of a display unit 4B.

FIGS. 13A to 13C are diagrams of the positional relation among shielding plates for shielding image display portions of respective display elements depending on in-focus positions A, B, and C in FIG. 6.

FIGS. 14 to 17 relate to a third embodiment of the present invention, FIG. 14 being a diagram of the entire structure of a stereoscopic endoscope system according to the third embodiment of the present invention.

FIG. 15 is a block diagram of the structure of a display control unit.

FIGS. 16A and 16B are diagrams explaining masked display screens of display elements, FIG. 16A showing a, case where one switch is operated twice, FIG. 16B showing a case where another switch is operated once.

FIG. 17 is a flowchart of the operation of a computing unit.

DETAILED DESCRIPTION OF THE PREFERRED EMBODIMENT(S)

Embodiments of the present invention will now be described below with reference to the drawings.

First Embodiment

A first embodiment of the present invention will now be described with reference to FIGS. 1 to 9.

Figure 1:
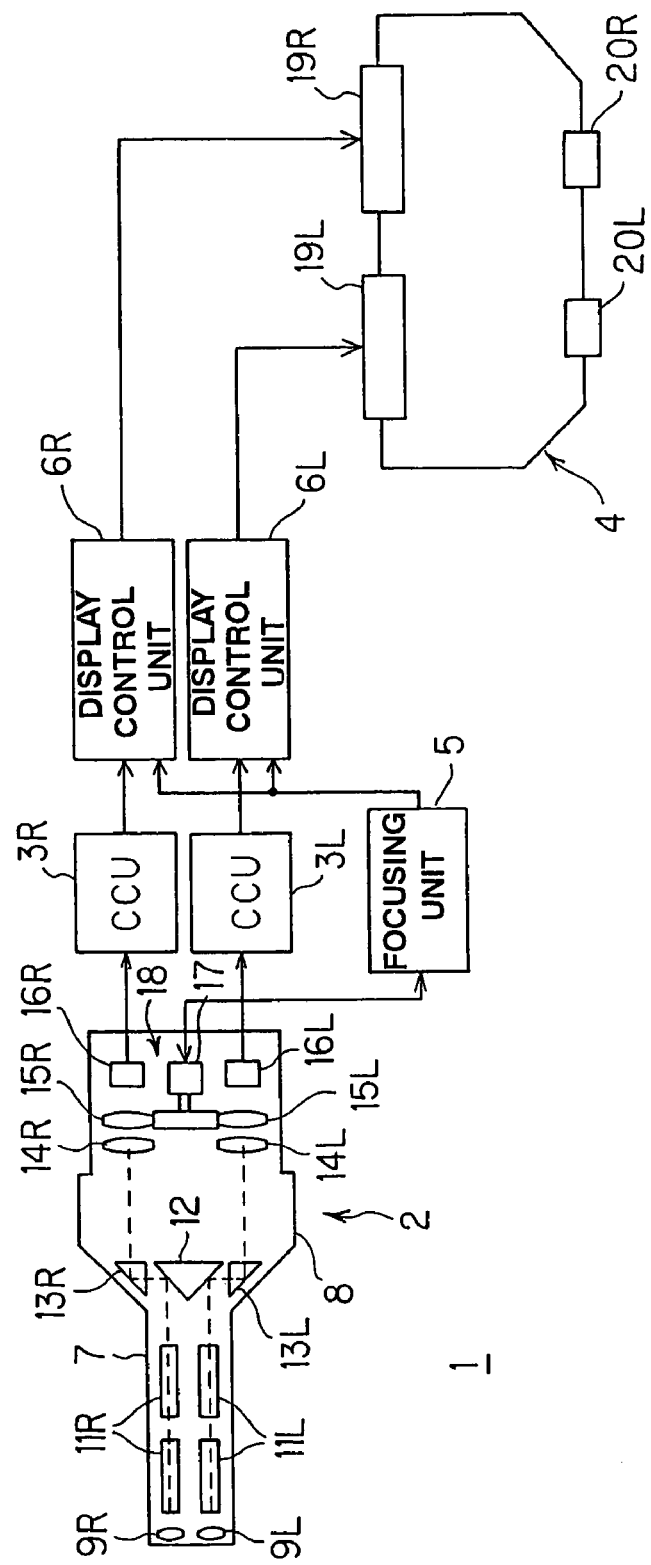

Referring to FIG. 1, according to the first embodiment of the present invention, a stereoscopic endoscope system 1 includes a stereoscopic endoscope 2 for stereoscopic image pickup, camera control units (hereinafter, CCUs) 3L and 3R for processing signals for CCDs built in the stereoscopic endoscope 2, a display unit 4 for displaying video signals generated by the CCUs 3L and 3R, a focusing unit 5 for driving a focusing mechanism in the stereoscopic endoscope 2 to perform focusing, and display control units 6L and 6R for display control, i.e., partially masking display elements, which actually display images, in the display unit 4 upon entering of video signals from the CCUs 3L and 3R and a count value corresponding to focusing by the focusing unit 5.

The stereoscopic endoscope 2 includes an insertion portion 7 which is elongated so as to be easily inserted into the body and a grasping portion 8 arranged at the proximal end of the insertion portion 7.

At the distal end of the insertion portion 7, objective lenses 9L and 9R are laterally arranged at a distance from each other so as to form optical images having a parallax. Left and right optical images are formed with a parallax by the objective lenses 9L and 9R. The formed left and right images are transmitted toward the rear along the insertion portion 7 through relay lens groups 11L and 11R.

Figure 19:
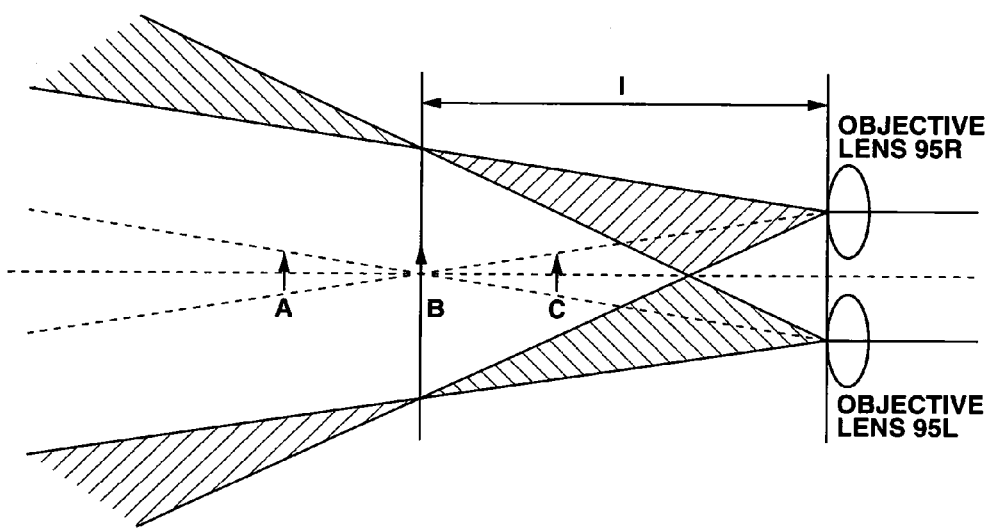
FIG. 19 is a diagram explaining observation ranges of right and left objective lenses, the ranges varying depending on the distance between an object and objective lenses (the position of the object).

For example, in observing an object in the position B in FIG. 19, the objective lenses 9L and 9R are set so as to center the object in each observation range (such that the images match with each other except the difference therebetween due to a parallax).

The left and right optical images transmitted backward through the relay lens groups 11L and 11R are guided to separate optical paths through a common prism 12 and subsequent prisms 13L and 13R arranged laterally. After that, the optical images are formed on CCDs 16L and 16R laterally arranged at a distance from each other after passing through left and right image forming lenses 14L and 14R and left and right focusing lenses 15L and 15R, respectively.

The grasping portion 8 has therein a focusing mechanism 18 in which a focusing motor 17 is rotated by the focusing unit 5 to move the focusing lenses 15L and 15R forward or backward such that the left and right optical images of the object at a predetermined distance are respectively brought into focus and formed on the CCDs 16L and 16R. The grasping portion 8 is adjusted by the focusing unit 5. The amount of movement of the focusing motor 17 is inputted to each of the display control units 6L and 6R.

The display control units 6L and 6R also receive video signals which are generated by processing output signals of the CCDs 16L and 16R. The display control units 6L and 6R partially mask video signals inputted from the CCUs 3L and 3R in accordance with the shift of the object position from the position B in FIG. 19 in response to a signal corresponding to the distance inputted from the focusing unit 5 to generate the masked video signals and then output the signals to left and right display elements 19L and 19R in the display unit 4. Thus, the left and right display elements 19L and 19R display left and right images picked up by the CCDs 16L and 16R, respectively.

An operator views through left and right eyes and left and right eyepiece sections 20L and 20R to observe the left and right images displayed on the left and right display elements 19L and 19R through eyepiece lenses (not shown) or the like, thus allowing the operator to stereoscopically view the object.

Figure 3:
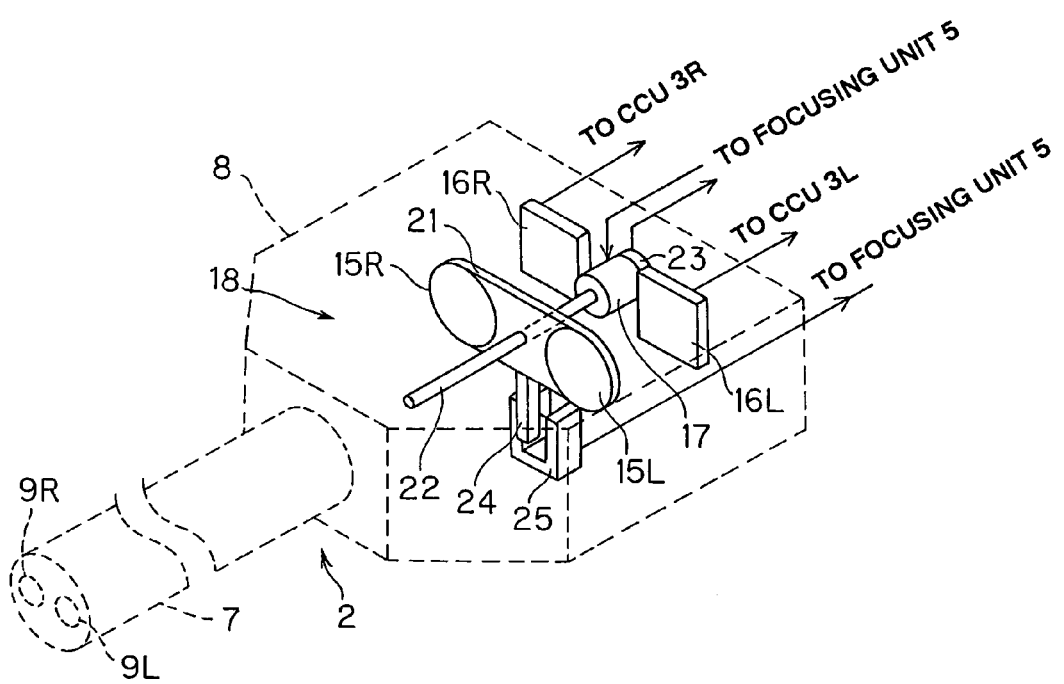

FIG. 3 shows the focusing mechanism 18 arranged in the grasping portion 8.

The left and right focusing lenses 15L and 15R are attached to a lens holding member 21. The lens holding member 21 is moved along a rotating shaft of the focusing motor 17 by the rotation of the focusing motor 17, so that the left and right focusing lenses 15L and 15R are simultaneously moved along the respective optical axes.

For example, a long ball screw 22 is attached to the rotating shaft of the focusing motor 17. The ball screw 22 is screwed into a screw hole in the lens holding member 21. The movement of the lens holding member 21 is restricted such that the member is moved along a guide shaft (not shown) arranged in parallel to the ball screw 22. As mentioned above, therefore, the rotation of the focusing motor 17 makes the left and right focusing lenses 15L and 15R to simultaneously move along the respective optical axes. The focusing motor 17 is rotated a motor rotation signal being applied from a motor driver 31 arranged in the focusing unit 5.

An encoder 23 is attached to the focusing motor 17. The encoder 23 detects the amount of rotation of the focusing motor 17, i.e., the amount of movement of the focusing lenses 15L and 15R and transmits a detected signal (encode signal) to a counter circuit 32 (see FIG. 2) in the focusing unit 5.

The lens holding member 21 has a projection 24, which moves along the axial direction of the ball screw 22 simultaneously with the movement of the lens holding member 21. In the grasping portion 8, a photosensor 25, serving as, e.g., a photointerrupter, is arranged as a position detector for detecting the position of the projection 24.

The attachment position of the photosensor 25 is adjusted as follows: When the photosensor 25 detects the projection 24, the focal distance corresponds to the distance between the object and the objective lenses 9L and 9R, so that left and right object images can be observed such that they match with each other.

A signal generated when the photosensor 25 detects the projection 24 is used as a signal to reset the counter circuit 32 in the focusing unit 5. Consequently, when the photosensor 25 detects the projection 24, a count value of the counter circuit 32 can be set to zero.

Figure 2:
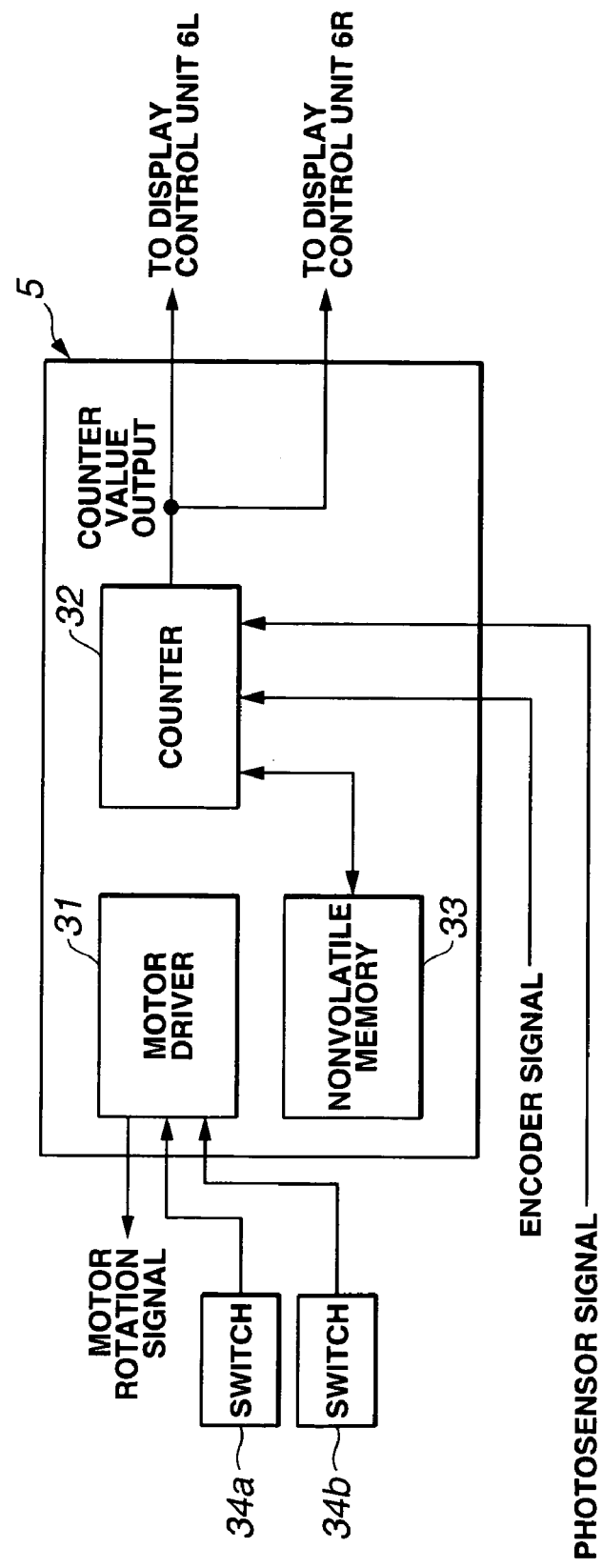

As shown in FIG. 2, the focusing unit 5 includes the motor driver 31 for rotationally driving the focusing motor 17, the counter circuit 32 for measuring the distance to an object, and a nonvolatile memory 33, such as a flash memory, for storing a count value counted by the counter circuit 32 when the focusing unit 5 is turned off.

The focusing unit 5 also includes switches 34a and 34b for instructing on focus control. For example, when the switch 34a is operated, the motor driver 31 outputs a motor rotation signal to rotate the focusing motor 17 so that an object in the position A in FIG. 18 comes into focus. When the switch 34b is operated, the motor driver 31 outputs a motor rotation signal to rotate the focusing motor 17 so that an object in the position C in FIG. 18 comes into focus.

The counter circuit 32 counts an encoder signal (encode output) from the encoder 23 which detects the amount of rotation of the focusing motor 17 and outputs a count value from the output terminal to the display control units 6L and 6R and the nonvolatile memory 33.

The counter circuit 32 is reset by a photosensor signal from the photosensor 25.

Data obtained by the counter circuit 32 is stored in the nonvolatile memory 33 such that the stopping position of the focusing motor 17 when the focusing unit 5 is turned off can be stored. When powered on, data stored in the nonvolatile memory 33 is preset into the counter circuit 32 so that the rotating position of the focusing motor 17 or the set positions of the focusing lenses 15L and 15R can be detected (counted) without being influenced by the turn-on or turn-off and a count value can be output to each of the display control units 6L and 6R.

Alternatively, the nonvolatile memory 33 may be omitted. In this case, the focusing motor 17 is activated at power-on and is moved forward or backward until the photosensor 25 detects the projection 24, thus detecting zero. Thus, an initial position may be detected (and the subsequent operation may be performed).

Instead of the photosensor 25 and the projection 24, a switch and a switch contact member may be used. The attachment positions of the photosensor 25 and the projection 24 may be set to maximum and minimum points (one end and the other end) in a movable range of the focusing motor 17.

Figure 4:
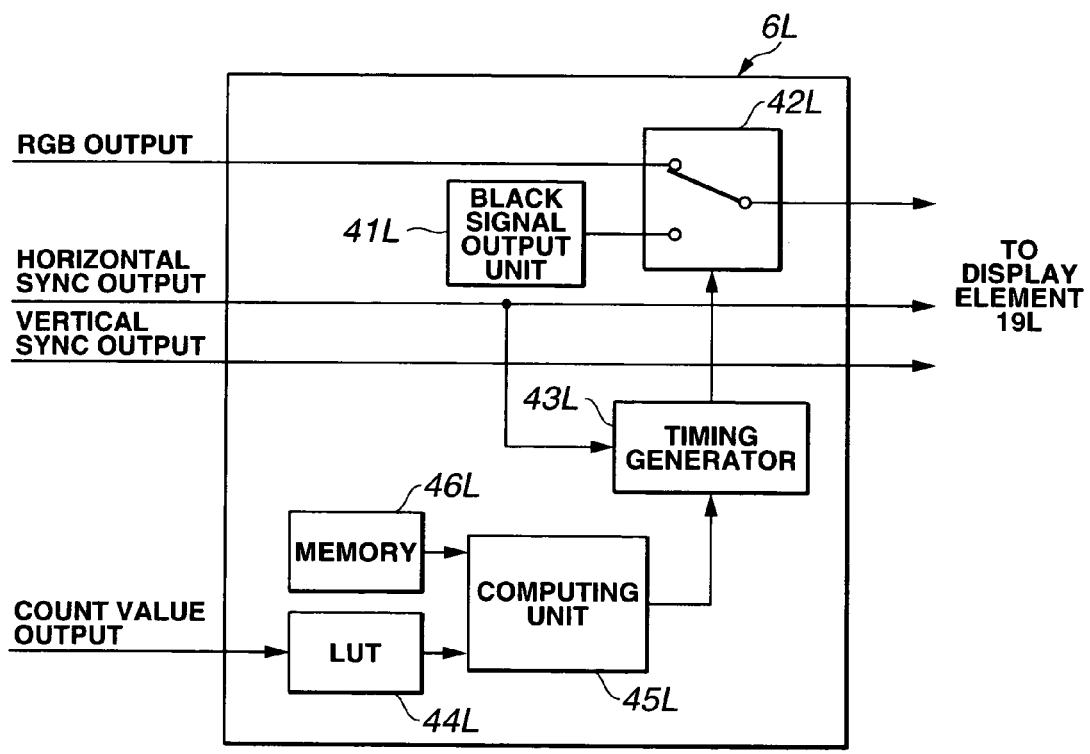

FIG. 4 shows the structure of the display control unit 6L. The display control unit 6R has the same structure as that of the display control unit 6L. The same components as those of the display control unit 6L are designated by the same reference numerals each including character "R" instead of "L".

The display control unit 6L includes a black signal output unit 41L for outputting, e.g., a black signal as a masking signal for masking. The black signal is inputted together with an RGB signal, serving as a video signal output from the CCU 3L, to a selector switch 42L.

Switching the selector switch 42L is controlled by a timing generator 43L.

On the other hand, a count value output from the focusing unit 5 is inputted to a lookup table (hereinafter, abbreviated to LUT) 44L arranged in the display control unit 6L. The LUT 44L reads out information corresponding to a count value, i.e., information regarding the distance between the object and the objective lens 9L and then outputs the information to a computing unit 45L.

The focusing unit 5 also includes a memory 46L for storing a reference distance where the object can be observed without mismatch through the left and right objective lenses 9L and 9R, i.e., the distance from the objective lenses to the position B in FIG. 19. Data regarding the reference distance output from the memory 46L is also inputted to the computing unit 45L.

The computing unit 45L calculates the difference between data regarding the reference distance in the memory 46L and data regarding an actually set distance and outputs data regarding the difference to the timing generator 43L.

The timing generator 43L also receives a horizontal synchronization (sync) signal from the CCU 3L. As will be described with reference to FIGS. 7A and 7B, the timing generator 43L counts clocks (not shown) synchronously with the horizontal sync signal in response to an output signal of the computing unit 45L for a video signal display period between the horizontal sync signals, thus determining timing to satisfy a relational expression, e.g., Expression (1), which will be described later. The timing generator 43L switches the selector switch 42L to output a black signal.

Figures 20A, 20B, 20C:
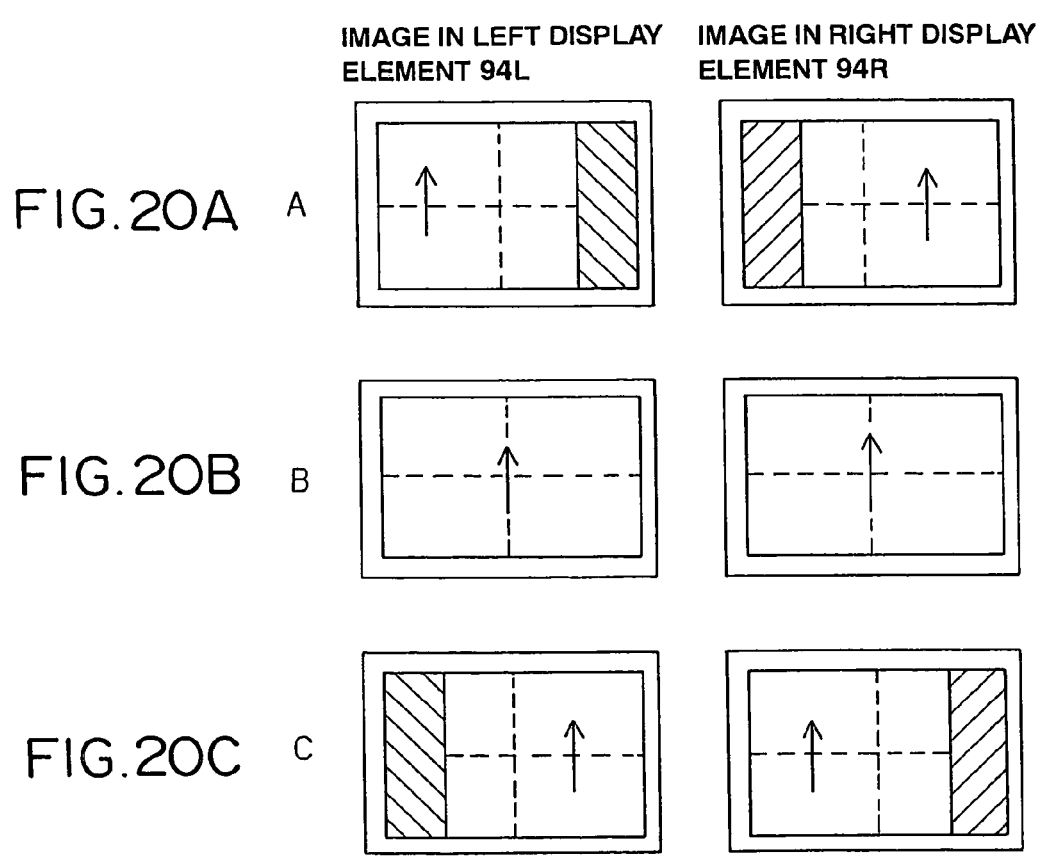
FIGS. 20A to 20C are diagrams of images displayed in right and left display elements, the images being obtained when objective lenses are focused on positions A, B, and C in FIG. 19, respectively.

As shown in FIG. 20B, when the object is located in the position B, the selector switch 42L is not switched to output a black signal. As shown in FIGS. 20A and 20C, when video signals, corresponding to image pickup areas that are not observed in common by both the left and right objective lenses, are output to the display elements 19L and 19R, the selector switch 42L in the focusing unit 5 is switched to select the black signal output unit 41L as will be described with reference to FIGS. 7A and 7B. Thus, display control is performed such that the image pickup areas that are not observed in common are masked in black and only an image pickup area that is observed in common by both the objective lenses is displayed, in the display element 19L. The display control unit 6R performs the similar display control to the display element 19R.

The operation according to the present embodiment will now be described below.

Figure 5:
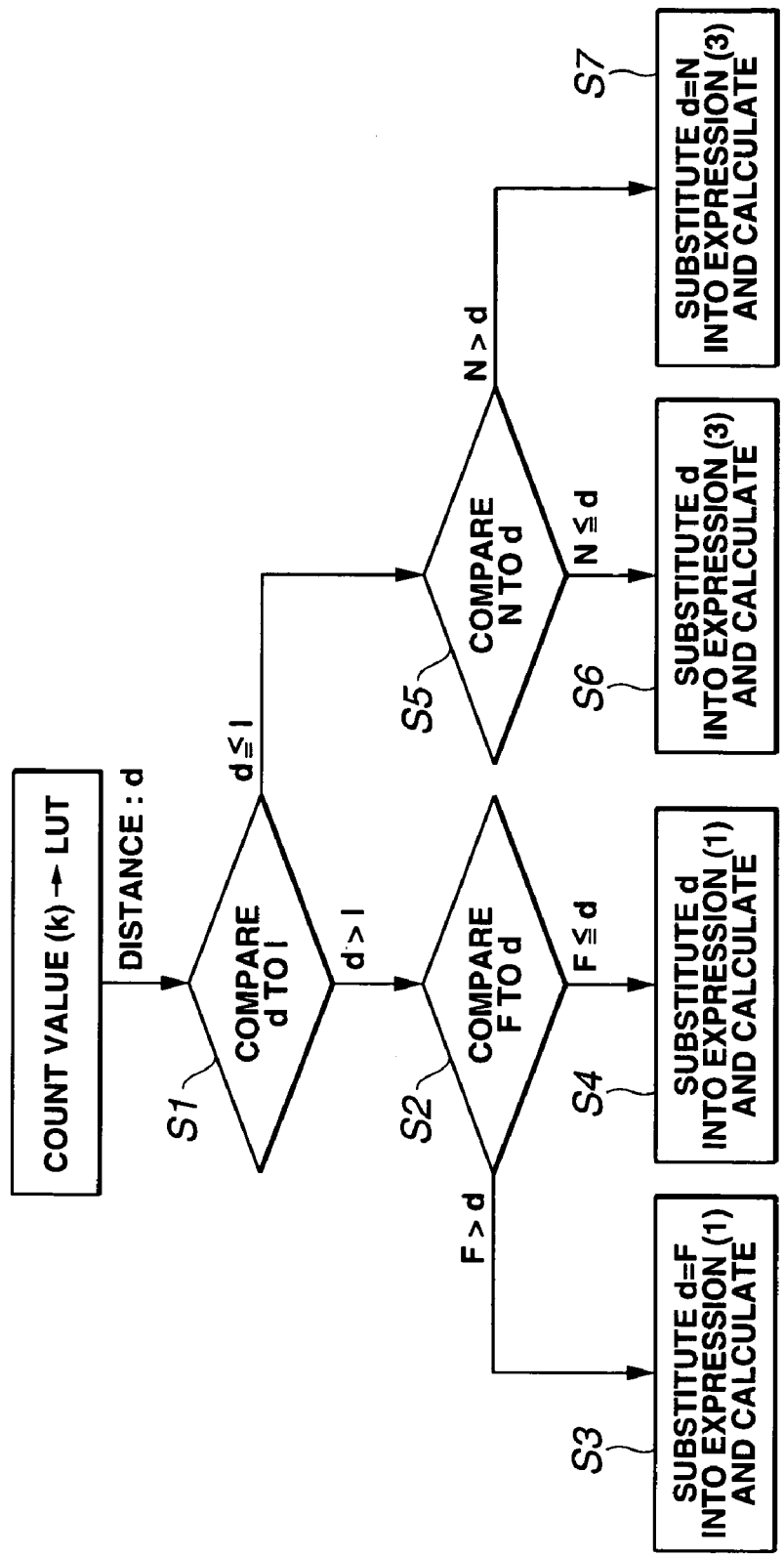

FIG. 5 shows a flowchart of the operation of the computing unit 45L.

First, a count value (k) is inputted to the LUT 44L, thus calculating a distance d between the objective lens 9L and an object. The distance d is inputted to the computing unit 45L. As shown in step S1, the computing unit 45L compares the distance d to a reference distance (distance between the objective lens 9L and the object in the position B in FIG. 19) 1 that is inputted from the memory 46L.

When d>1, as shown in step S2, the computing unit 45L compares the distance d to a threshold F, which corresponds to the distance to the farthest point. As for the threshold F, if the distance between the object and the objective lens 9L is longer than the threshold F, it is difficult to stereoscopically view images of the object.

As a result of the comparison, if F>d, as shown in step S3, d=F is substituted into Expression (1), which will be described later, and calculation is performed. A result of the calculation is output to the timing generator 43L.

If the comparison result indicates F≦d, as shown in step S4, d is substituted into Expression (1), which will be described below, and calculation is performed. The calculation result is output to the timing generator 43L.

On the other hand, if the comparison result in step S2 indicates that d≦1, as shown in step S5, the distance d is compared to a threshold N, which corresponds to the distance to the nearest point. As for the threshold N, if the distance between the object and the objective lens 9L is shorter than the threshold d, it is difficult to stereoscopically view images of the object.

If the comparison result indicates that n≦d, as shown in step S6, d is substituted into Expression (3), which will be described below, and calculation is performed. A result of the calculation is output to the timing generator 43L.

If N>d, as shown in step S7, d=N is substituted into Expression (3), which will be described below, and calculation is performed. A result of the calculation is output to the timing generator 43L.

As mentioned above, in order to prevent an image to be displayed from being excessively masked when the objective lens 9L is too close to the object and when the objective lens 9L is too far from the object, information regarding the nearest point and that regarding the farthest point are previously set and the pieces of information are stored in the memory 46L so that black is not output even when the objective lens comes closer to the object than the nearest point or goes farther from the object than the farthest point.

The operation of switching the selector switch 42L by the timing generator 43L which receives an output signal of the computing unit 45L will now be described with reference to FIGS. 6, 7A, and 7B.

Figure 6:
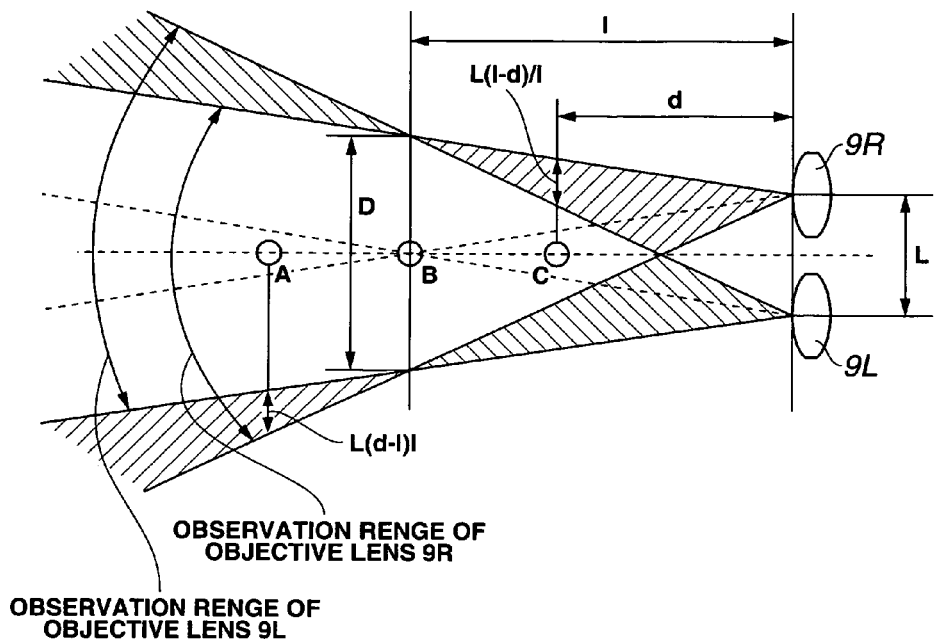

FIG. 6 shows the details of the relation between the objective lenses 9L and 9R whose observation ranges (image forming ranges) vary depending on an object and the position of the object (distance to the object).

Figure 18:
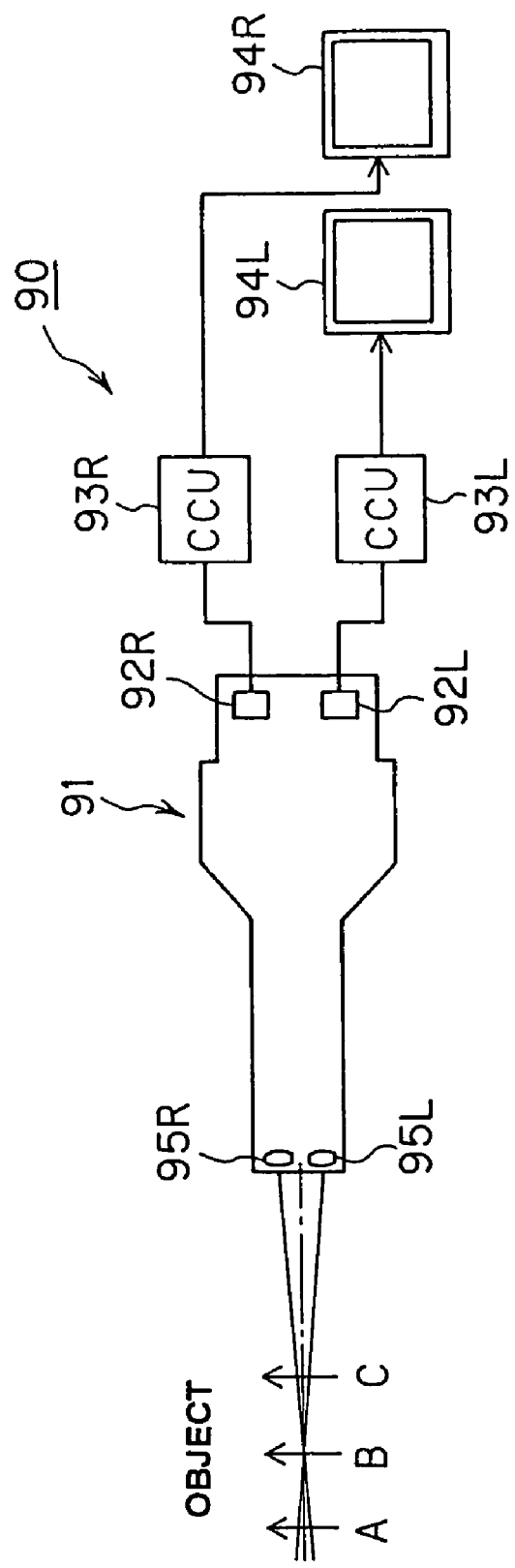
FIG. 18 is a schematic diagram of the structure of a conventional stereoscopic endoscope.

Similar to the description with reference to FIG. 18, when the object is located in the position B relative to the objective lenses 9L and 9R, i.e., the reference distance 1 is obtained, the objective lenses 9L and 9R have a common (the same) observation range and there is no areas that are not observed by both the lenses. Optical images, corresponding to the respective observation ranges, obtained through the objective lenses 9L and 9R are electrically converted through the CCDs 16L and 16R, respectively. The electrically converted optical images are inputted to the CCUs 3L and 3R, respectively. After that, the display elements 19L and 19R display respective images corresponding to the same observation range (display range), respectively.

On the other hand, if the object is located in the position A where the distance d is longer than that in the position B (d>1), alternatively, when the object is located in the position C where the distance d is shorter than that in the position C (d<1), the observation range of the objective lens 9L is different from that of the objective lens 9R.

Shaded areas correspond to image pickup areas that are not observed in common in both of the left and right display elements 19L and 19R.

Let L be the distance between the objective lenses 9L and 9R. Assuming that the observation ranges of the objective lenses 9L and 9R coincide with each other when the distance between the object and the objective lenses 9L or 9R is the reference distance 1 as shown in FIG. 6, the following relational expressions can be obtained using similar relations.

(A) Position A (when d>1)

The lateral length (or horizontal length upon display) of an area that is observed by the right objective lens 9R but is not observed by the left objective lens 9L, alternatively, the lateral length (horizontal length) of an area that is observed by the left objective lens 9L but is not observed by the right objective lens 9R is expressed as follows:

$$L(d-l)/l.$$

The total length in the lateral direction of the observation range is expressed as follows:

$$Dd/l.$$

As shown in FIGS. 7A and 7B, time t required to display the entire observation range corresponds to horizontal sync time 1H excluding front porch and back porch. FIG. 7A shows timings for output signals from the timing generators 43 (for allowing to output black signals) to the left and right display elements 19L and 19R when the object is located in the position A. FIG. 7B shows timings for output signals from the timing generators 43 (for allowing to output black signals) to the left and right display elements 19L and 19R when the object is located in the position C.

Time when the left display element 19L starts displaying the horizontal length of the image pickup area that is not observed in common, i.e., the area which is not observed in the right display element 19R is expressed as follows.

$$\{1-L(d-l)/Dd\}t \quad (1)$$

End time is just before the front porch.

The timing generator 43L outputs a switching signal at the above timing. The selector switch 42L is switched in response to the output.

Time when the right display element 19R starts displaying the horizontal length of the image pickup area that is not observed in common in both the display elements is just after the back porch. End time to display the above length is expressed as follows.

$$\{L(d-l)/Dd\}t \quad (2)$$

Similarly, the timing generator 43R outputs a switching signal at the above timing. The selector switch 42R is switched in response to the output.

(B) Position C (when d<l)

The length of an area that is observed by the left objective lens 9L but is not observed by the right objective lens 9R is expressed as follows:

$$L(l-d)/l.$$

The total length of the observation range is expressed as follows:

$$Dd/l.$$

Similarly, let t be time required to display the entire range. Time when the left display element 19L starts displaying the length of the image pickup area that is not observed in common in both the display elements is just after back porch. End time is expressed as the following expression.

$$\{L(l-d)/Dd\}t \quad (3)$$

The timing generator 43L outputs a switching signal at the above timing. The selector switch 42L is switched in response to the output.

On the other hand, time when the right display element 19R starts displaying the length of the image pickup area that is not observed in common in both the display elements is expressed as the following expression.

$$\{1-L(l-d)/Dd\}t \quad (4)$$

End time is just before front porch.

Similarly, the timing generator 43R outputs a switching signal at the above timing. The selector switch 42R is switched in response to the output.

In this manner, an area of which image is picked up by the right objective lens 9R but is not observed by the left objective lens 9L and another area of which image is not picked up by the right objective lens 9R but is observed by the left objective lens 9L can be masked in black by outputting black signals for the corresponding timings. In masking, white may be used instead of black. Another color may be output.

The present embodiment provides the following advantages.

An area of which image is picked up by the left CCD 16L but is not picked up by the right CCD 16R and another area of which image is not picked up by the left CCD 16L but is picked up by the right CCD 16R, i.e., image pickup areas that are not observed in common by both the CCDs are not displayed in order to prevent the left and right eyes of an observer from viewing different images. Thus, images corresponding to the same observation range can be displayed in the display elements 19L and 19R, respectively.

Since only the same observation range is displayed in each of the left and right display elements 19L and 19R, endoscopic images which allow the operator to easily obtain stereoscopic vision can be provided. Even when exacting tasks are needed, therefore, surgery can be smoothly performed based on images which easily permit stereoscopic viewing. In addition, eyestrain or operator fatigue, which is caused when portions observed through either objective lenses are displayed, can be remarkably reduced.

In other words, an environment where the operator easily performs endoscopy and the like can be provided.

Figure 8:
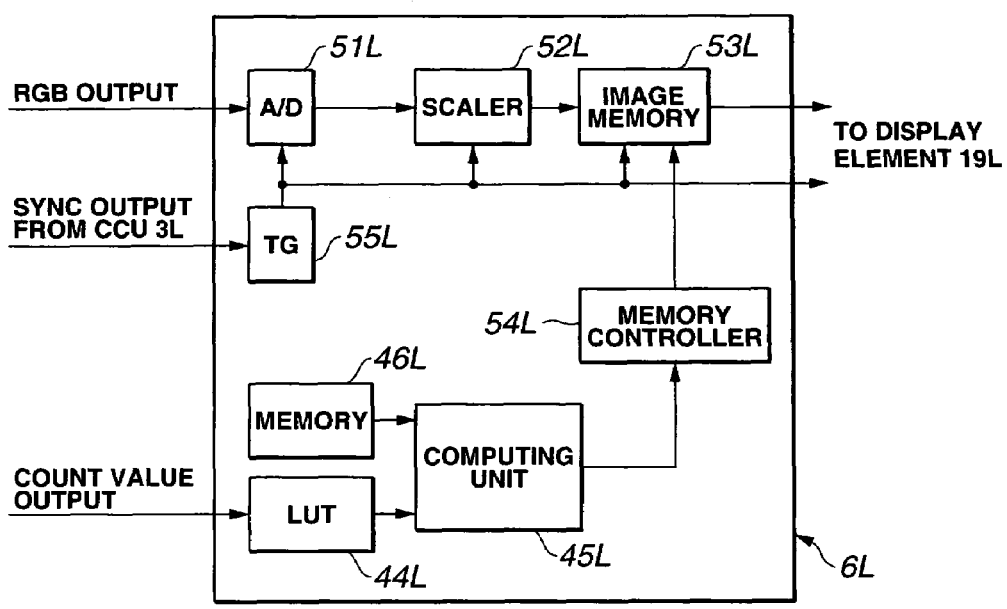

The structure of the display control unit 6L for switching the selector switch 42L in an analog manner has been described with reference to FIG. 4. FIG. 8 shows a modification of the first embodiment. According to the modification, a display control unit 6L may be designed so as to perform masking control in a digital manner.

In the display control unit 6L according to the modification in FIG. 8, an analog RGB signal output from a CCU 3L is inputted to an AD conversion circuit 51L and is converted into a digital RGB signal therethrough. After that, the digital signal is inputted to a scaler circuit 52L and is subjected to processing, e.g., pixel interpolation, thus producing image data in a display format for a display element 19L. Image data of one frame is stored in an image memory 53L.

A memory controller 54L reads and writes image data from/to the image memory 53L.

A sync signal output from the CCU 3L is inputted to a timing generator (hereinafter, abbreviated to TG) 55L. The TG 55L generates operation clocks for the AD conversion circuit 51L, the scaler circuit 52L, and the image memory 53L on the basis of the sync signal.

Similar to the case in FIG. 4, the display control unit 6L includes a memory 46L which stores information regarding the distance between an object and objective lenses 9R and 9L where right and left object images can be viewed without mismatch, an LUT 44L which previously stores information regarding the relation between the objective lenses 9L and 9R and the object so as to output the distance therebetween in response to an output value of a counter circuit 32, and a computing unit 45L for comparing an output value of the memory 46 with an output value of the LUT 44L to output the comparison result to the memory controller 54L.

When the comparison output of the computing unit 45L is a signal indicating that masking is not needed, the memory controller 55L reads out a video signal which has been output from the scaler circuit 52L and been stored in the image memory 53L. When the comparison output of the computing unit 45L is a signal indicating that masking is needed, the memory controller 55L allows to output a mask signal.

An output of the image memory 53L and an output of the TG 55L are inputted to the display element 19L.

In the display control unit 6L in FIG. 4, the timing generator 43L switches the selector switch 42L so that a signal of the black signal output unit 41L is output at masking timing. In the display control unit 6L in FIG. 8, the memory controller 54L designates an address signal in the image memory 53L so that a mask signal is output at masking timing.

For example, the image memory 53L includes an area to store video signals output from the scaler circuit 52L and a mask signal storage area in which mask signals to mask an image in black are stored in advance. The areas have different addresses.

In accordance with a signal indicating the comparison result output from the computing unit 45L, a video signal is read from the area for storing video signals or a mask signal is read from the mask signal storage area.

Figure 9:
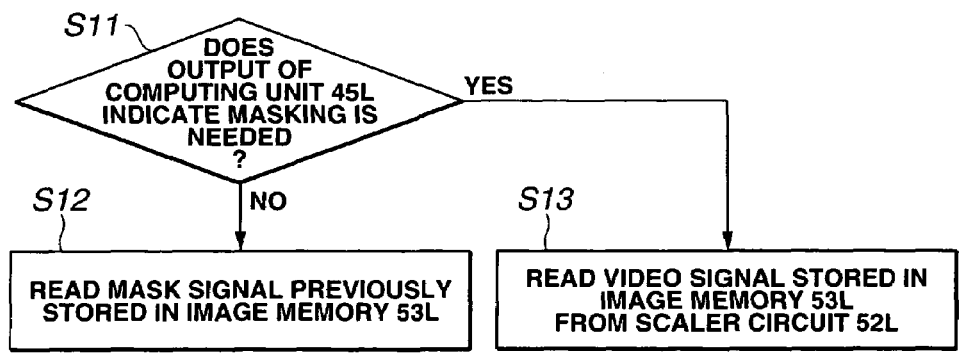

Therefore, the operation of the memory controller 54L in this case will be performed as shown in FIG. 9.

In other words, as shown in step S11, it is determined whether an output from the computing unit 45L needs masking (this state is simply described as ON in FIG. 9) or not (this state is simply described as OFF in FIG. 9).

As shown in step S12, if the comparison result indicates that masking is needed, the memory controller 54L reads out a mask signal stored in the image memory 53L.

On the other hand, if the comparison result indicates that masking is not needed, the memory controller 54L reads out a video signal stored in the image memory 53L from the scaler circuit 52L. Advantages obtained using the display control unit 6L of FIG. 8 are substantially the same as those using the display control unit 6L of FIG. 4.

The switches 34a and 34b for performing the instruction operation to adjust the focal distance may be arranged in the grasping portion 8 of the stereoscopic endoscope 2 instead of in the focusing unit 5. Alternatively, the switches 34a and 34b may be designed as foot switches. When the operator steps on the footswitches, the focusing lenses 15L and 15R are moved forward or backward through the motor driver 31 such that the focal distance can be variably set.

Second Embodiment

A stereoscopic endoscope system according to a second embodiment of the present invention will now be described with reference to FIGS. 10 to 14.

Figure 10:
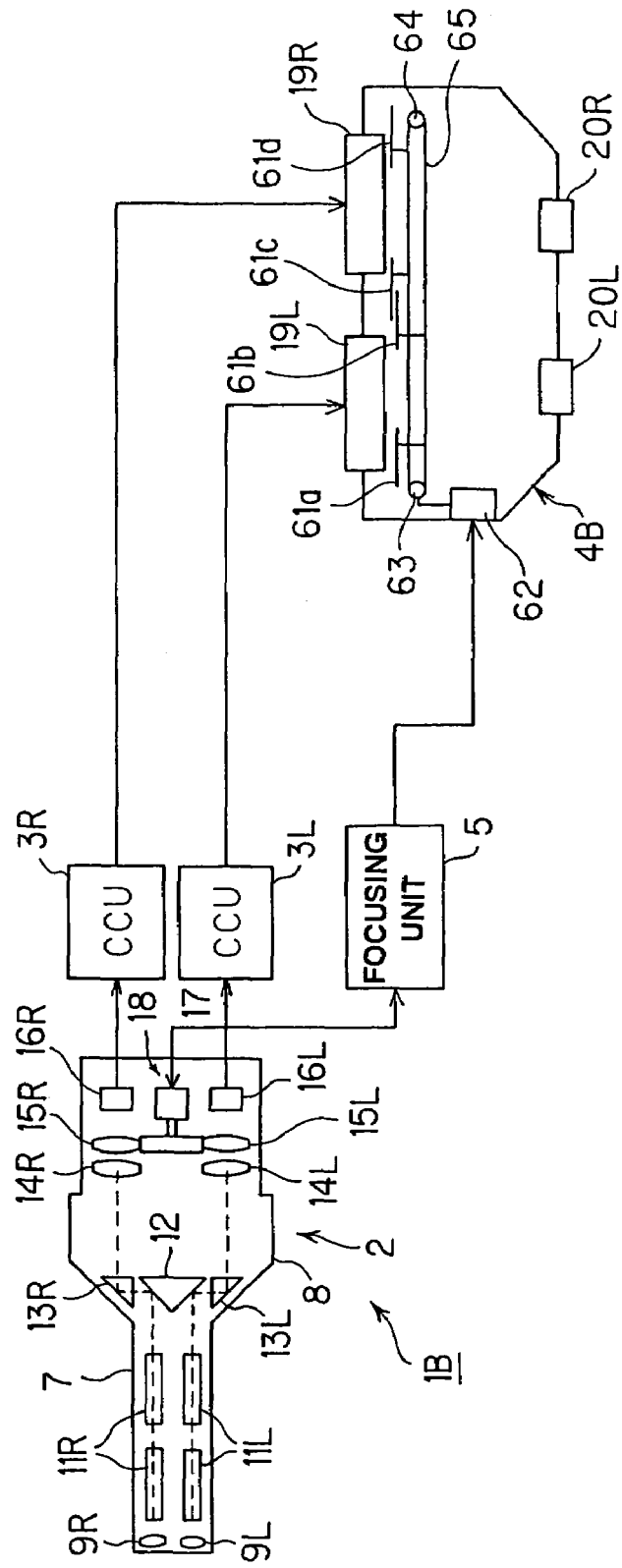

FIG. 10 shows the entire structure of a stereoscopic endoscope system 1B according to the second embodiment of the present invention. The stereoscopic endoscope system 1B has a display unit 4B which includes the shielding plates 61a, 61b, 61c, and 61d instead of the display control units 6L and 6R for electrical masking in the stereoscopic endoscope system 1 of FIG. 1. The display unit 4B controls the amount of movement of each of the shielding plates (or light shielding plates) 61a to 61d, each having a light shielding function, via a shielding plate control unit 62, on the basis of an output of a focusing unit 5, thus mechanically shielding (masking) a display image portion which is displayed in only any one of display elements 19L and 19R (i.e., the portion which is not displayed in the other one).

Therefore, the stereoscopic endoscope system 1B includes a stereoscopic endoscope 2 for stereoscopic image pickup, CCUs 3L and 3R for processing signals of CCDs arranged in the stereoscopic endoscope 2, the display unit 4B for displaying video signals generated by the CCUs 3L and 3R, the focusing unit 5 for driving a focusing mechanism arranged in the stereoscopic endoscope 2 to perform focusing. The stereoscopic endoscope system 1B further comprises the shielding plate control unit 62 for performing display control by masking display elements 19L and 19R, which are arranged in the display unit 4B and actually display images, using the shielding plates 61a, 61b, 61c, and 61d, which are arranged close to eyepiece sections 20L and 20R in front of the display elements 19L and 19R, in accordance with a count value corresponding to focusing received from the focusing unit 5.

In the stereoscopic endoscope system 1B according to the present embodiment, the stereoscopic endoscope 2, the CCUs 3L and 3R, and the focusing unit 5 have the same structures as those according to the first embodiment, respectively. Video signals output from the CCUs 3L and 3R are inputted to the display elements 19L and 19R in the display unit 4B. The display elements 19L and 19R display the received video signals.

Figure 11:
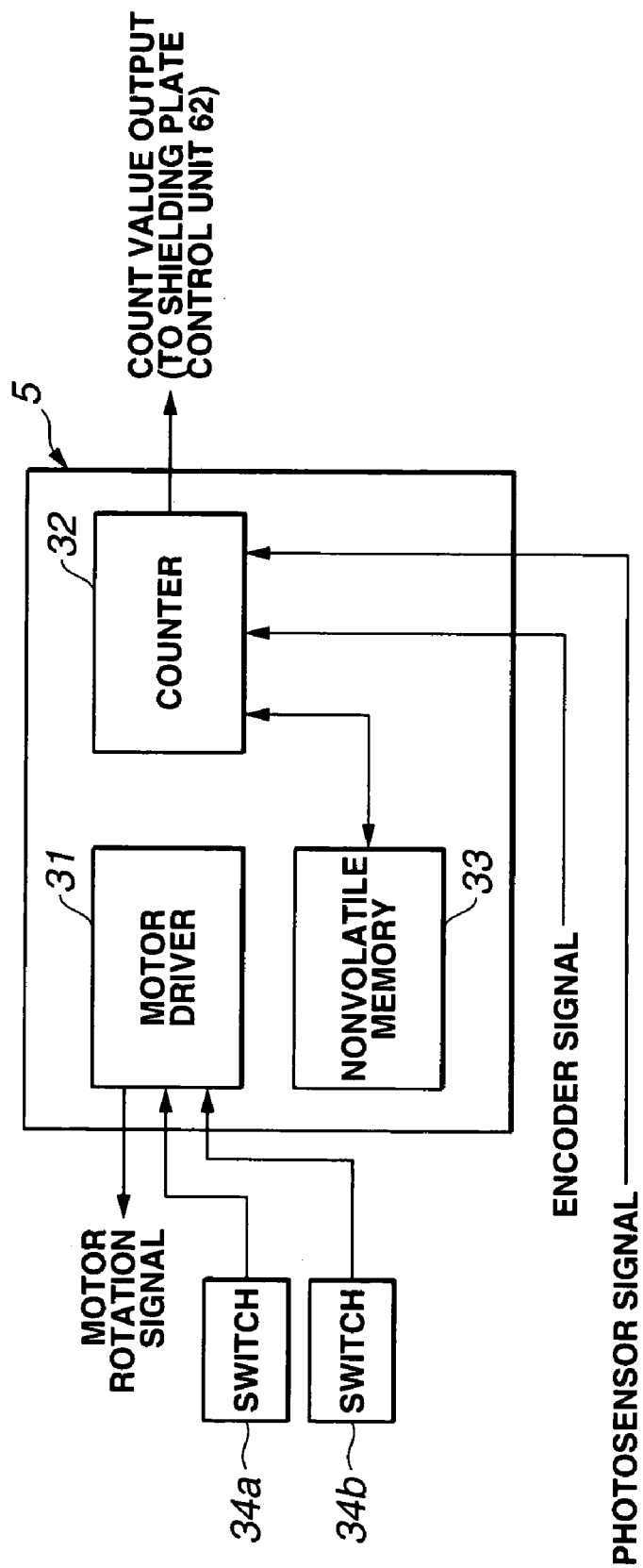

As shown in FIG. 11, the focusing unit 5 according to the present embodiment differs from that according to the first embodiment with respect to a point that a count value, corresponding to the amount of movement of a focusing motor 17, output from a counter circuit 32, is inputted to the shielding plate control unit 62 provided in the display unit 4B. Accordingly, the same components as those in the first embodiment are designated by the same reference numerals and a description thereof is omitted.

Figure 12:
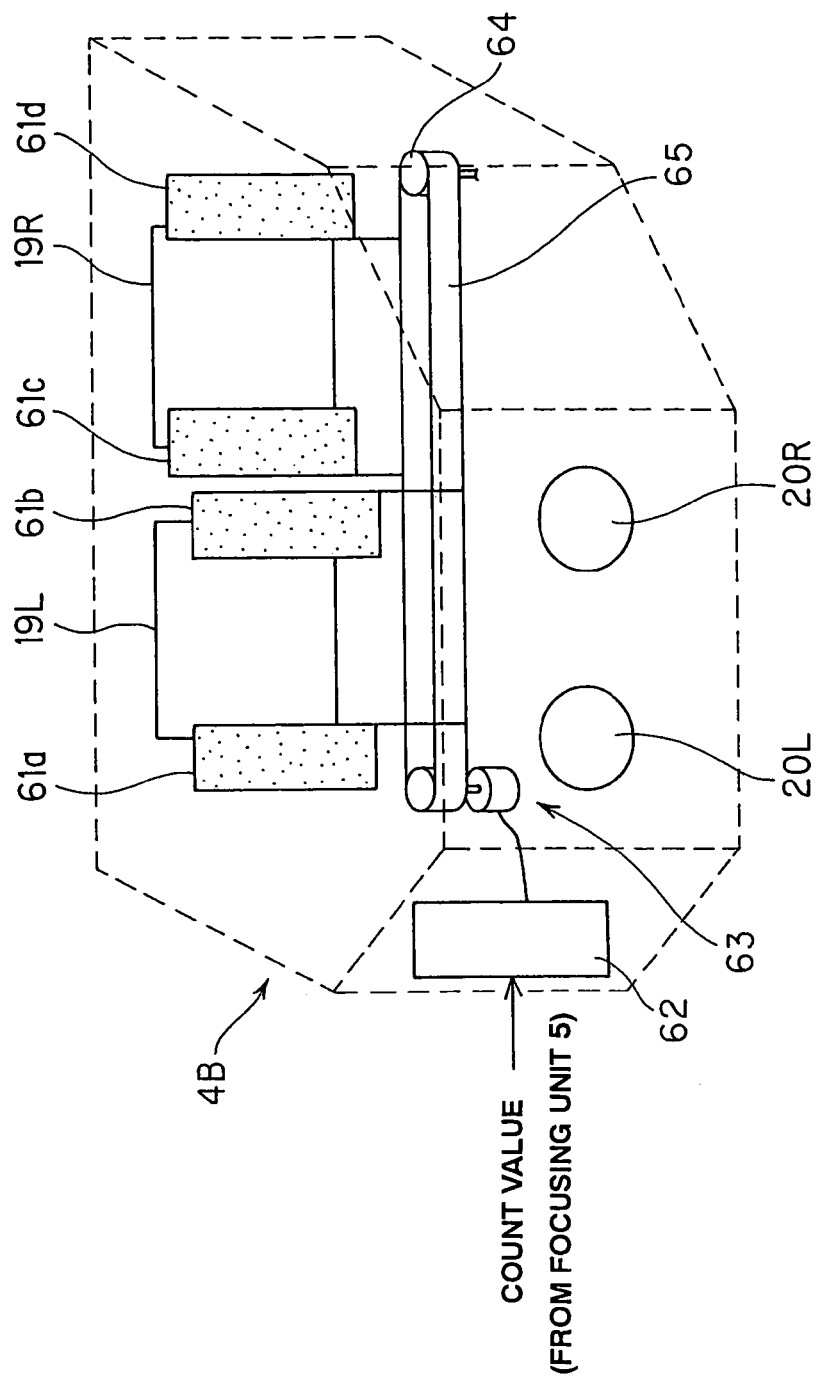

FIG. 12 shows the internal structure of the display unit 4B.

The display unit 4B includes the left and right display elements 19L and 19R for receiving left and right video signals from the CCUs 3L and 3R to display the left and right video signals, respectively, and the eyepiece sections 20L and 20R through which an operator peers the left and right display elements 19L and 19R in order to view left and right images using their left and right eyes. The display elements 19L and 19R face the eyepiece sections 20L and 20R, with eyepiece lenses (not shown) therebetween, respectively.

In front of the left and right display elements 19L and 19R, a motor 63 with a pulley, which is driven by the shielding plate control unit 62, and a pulley 64 are laterally arranged at a distance from each other. A belt 65 is stretched therebetween such that the belt 65 is movable by rotating the motor 63 with the pulley.

In front of the display element 19L in the belt 65, the pair of shielding plates 61a and 61b are attached in front of the belt 65 such that both the ends of the display element 19L appear to be positioned between the plates 61a and 61b. The other pair of shielding plates 61c and 61d are attached in front of the belt 65 such that both the ends of the display element 19R appear to be positioned between the plates 61c and 61d.

More specifically, the shielding plates 61a and 61b are attached to this side of the belt 65 (i.e., the side of the eyepiece sections 20L and 20R) and the shielding plates 61c and 61d are attached to the forward side of the belt 65 (i.e., the side of the display elements 19L and 19R).

When the belt 65 travels, the shielding plates 61a and 61b shield (mask) an image displayed in the display element 19L and the shielding plates 61c and 61d shield (mask) an image displayed in the display element 19R in accordance with the traveling direction.

More specifically, when the motor 63 with the pulley rotates clockwise, the shielding plates 61a and 61b move to the left. When the motor 63 with the pulley rotates counterclockwise, the shielding plates 61a and 61b move to the right.

On the other hand, when the motor 63 with the pulley rotates clockwise, the shielding plates 61c and 61d move to the right. When the motor 63 with the pulley rotates counterclockwise, the shielding plates 61c and 61d move to the left.

Figure 13A:
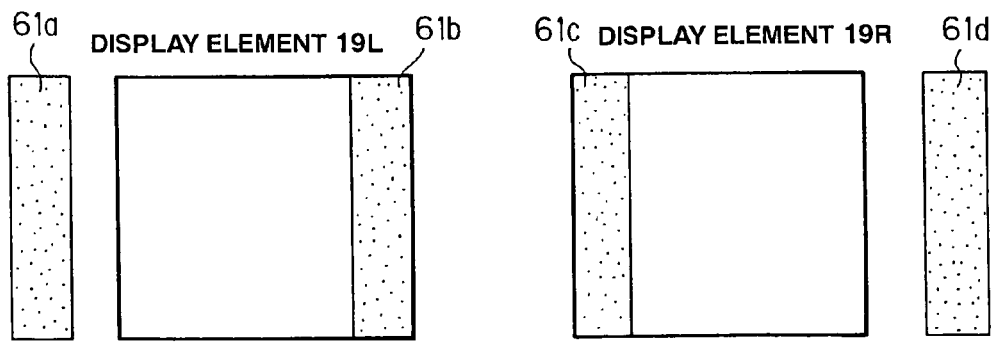
Figure 13B:
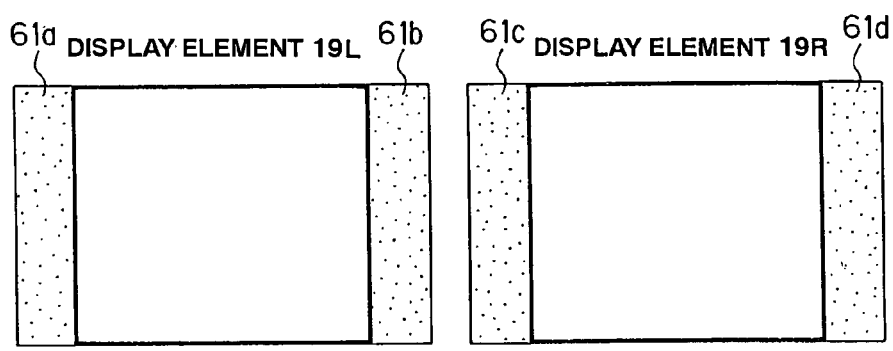

In reference observation mode in which the object in the position B in FIG. 6 is brought into focus, images displayed in the display elements 19L and 19R are not shielded by the shielding plates 61a, 61b, 61c, and 61d (see FIG. 13B). The whole images displayed in the display elements 19L and 19R can be observed through the eyepiece sections 20L and 20R, respectively.

Figure 13C:
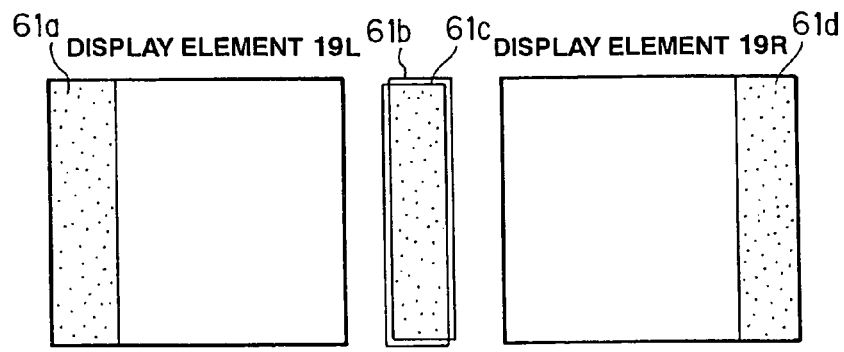

On the other hand, in observing the object in the position A or C in FIG. 6 is brought into focus, as shown in FIG. 13A or 13C, the inner portions of the display elements 19L and 19R or the outer portions thereof are shielded.

The shielding plate control unit 62 drives the motor 63 with the pulley in accordance with a count value of the counter circuit 32 in the focusing unit 5. The relation between the distance between the object and the objective lenses 9L and 9R and the corresponding count value of the counter circuit 32 is previously obtained. Information regarding the relation therebetween is stored in a memory (not shown) in the shielding plate control unit 62. When the object in the position A in FIG. 6 comes into focus, the motor 63 with the pulley is rotated counterclockwise in accordance with the count value of the counter circuit 32. When the object in the position C in FIG. 6 comes into focus, the motor 63 with the pulley is rotated clockwise in accordance with the count value.

A portion displayed in only the display element 19L is shielded by the shielding plates 61a or 61b and a portion display in only the display element 19R is shielded by the shielding plate 61c or 61d.

FIGS. 13A to 13C show the positional relations between the display elements 19L and 19R, and the shielding plates 61a, 61b, 61c, and 61d, in each position brought into focus.

When the object in the position A in FIG. 6 comes into focus, the inner portions of the display elements 19L and 19R are shielded by the shielding plates 61b and 61c, respectively.

The shielding plates 61a, 61b, 61c, and 61d are attached to the belt 65 so that when the object in the position B in FIG. 6 is in focus, the display elements 19L and 19R are not shielded by the shielding plates 61a, 61b, 61c, and 61d.

When the object in the position C in FIG. 6 is in focus, the outer portions of the display elements 19L and 19R are shielded by the shielding plates 61a and 61d, respectively.

A procedure for obtaining the rotating time of the motor 63 with the pulley will now be described.

It is assumed that the stereoscopic endoscope system 1B is designed such that ranges shown as the observation ranges of the objective lenses 9L and 9R are the same as image pickup ranges on the CCDs 16L and 16R and images picked up by the CCDs 16L and 16R are displayed in the display elements 19L and 19R each having a width W. Let $\omega$ be the rotating speed of the motor 63 with the pulley and let r be the radius of the pulley 64.

Position A (when d>l)

The horizontal length of an area that is observed by the right objective lens 9R but is not observed by the left objective lens 9L is expressed as follows.

$$L(d-l)/l$$

When the area is displayed in the display elements 19L and 19R each having the width W, the length is expressed as follows.

$$WL(d-l)/(Dl)$$

Since $r\omega$ denotes the traveling speed of the belt 65, a period of time during which the motor 63 with the pulley is driven is expressed as follows.

$$WL(d-1)/(Dlr\omega) \quad (5)$$

Position C (when d<l)

The horizontal length of an area that is observed by the right objective lens 9R but is not observed by the left objective lens 9L is expressed as follows.

$$L(l-d)/l$$

When the area is displayed in the display elements 19L and 19R each having the width W, the length is expressed as follows.

$$WL(l-d)/(Dl)$$

Since $r\omega$ denotes the traveling speed of the belt 65, a period of time during which the motor 63 with the pulley is driven is expressed as follows.

$$WL(l-d)/(Dlr\omega) \quad (6)$$

The motor 63 with the pulley is driven for the period of time (5), thus shielding the area which is displayed in the display element 19L but is not displayed in the display element 19R in order to prevent the area from being viewed. The motor 63 with the pulley is driven for the period of time (6), thus shielding the area which is displayed in the display element 19R but is not displayed in the display element 19L in order to prevent the area from being viewed.

The display elements 19L and 19R may be shielded in another color, e.g., white, instead of black. Alternatively, the display elements 19L and 19R are not shielded but the eyepiece sections 20L and 20R may be shielded.

The present embodiment has the following advantages.

In addition to the advantages according to the first embodiment, since the display control units 6L and 6R are not needed, the number of components can be reduced, thus producing the system at low cost.

Third Embodiment

A stereoscopic endoscope system according to a third embodiment of the present invention will now be described with reference to FIGS. 14 to 17. FIG. 14 shows the entire structure of a stereoscopic endoscope system 1C according to the third embodiment of the present invention. According to the present embodiment, an operator operates switches, thus masking displayed images in accordance with the operation.

The stereoscopic endoscope system 1C includes a focusing unit 5C and a display control unit 72. The focusing unit 5C is used to control a focusing motor 17 in the same way as the focusing unit 5 in the stereoscopic endoscope system 1 in FIG. 1 but does not output a count value to the display control units 6L and 6R. The display control unit 72 including switches 71a and 71b is arranged instead of the display control units 6L and 6R in FIG. 1.

Specifically, the stereoscopic endoscope system 1C includes a stereoscopic endoscope 2 for stereoscopic image pickup, CCUs 3L and 3R for processing signals of CCDs 16L and 16R arranged in the stereoscopic endoscope 2, the display control unit 72 which receives video signals produced by the CCUs 3L and 3R, a display unit 4 for displaying the video signals processed through the display control unit 72, and the focusing unit 5C for driving a focusing mechanism arranged in the stereoscopic endoscope 2 to perform focusing.

The CCUs 3L and 3R and the display unit 4 have the same structures as those in the first embodiment. The stereoscopic endoscope 2 does not need position detecting means, such as the encoder 23 and the photosensor 25 used to detect the rotational position of the motor 17, in the first embodiment.

Additionally, the focusing unit 5C includes a motor driver 31 and switches 34a and 34b, which are the same as those in the focusing unit 5 shown in FIG. 2 according to the first embodiment.

When the switch 34a is pressed, the motor 17 is rotated so as to bring the far point into focus. When the other switch 34b is pressed, the motor 17 is rotated so as to bring the near point into focus. Focusing on an arbitrary position between the far point and the near point can be performed.

Left and right optical images formed in the CCDs 16L and 16R on the respective focal points are electrically converted through the CCDs 16L and 16R, respectively. Output signals of the CCDs 16L and 16R are transmitted to the CCUs 3L and 3R, respectively. The CCUs 3L and 3R convert the signals into video signals to be displayed in the display elements 19L and 19R, respectively. After that, the video signals are transmitted to the display control unit 72.

The display control unit 72 outputs the video signals inputted from the CCUs 3L and 3R to the display elements 19L and 19R, respectively. In addition, the display control unit 72 partially superimposes masking signals (to mask the video signals) on the video signals to be displayed in the display elements 19L and 19R in accordance to the operation for the switches 71a and 71b and outputs the resultant signals to the display elements 19L and 19R.

In the display unit 4, an observer views images displayed in the display elements 19L and 19R from eyepiece sections 20L and 20R through an optical system (not shown) in the display unit 4.

Figure 15:
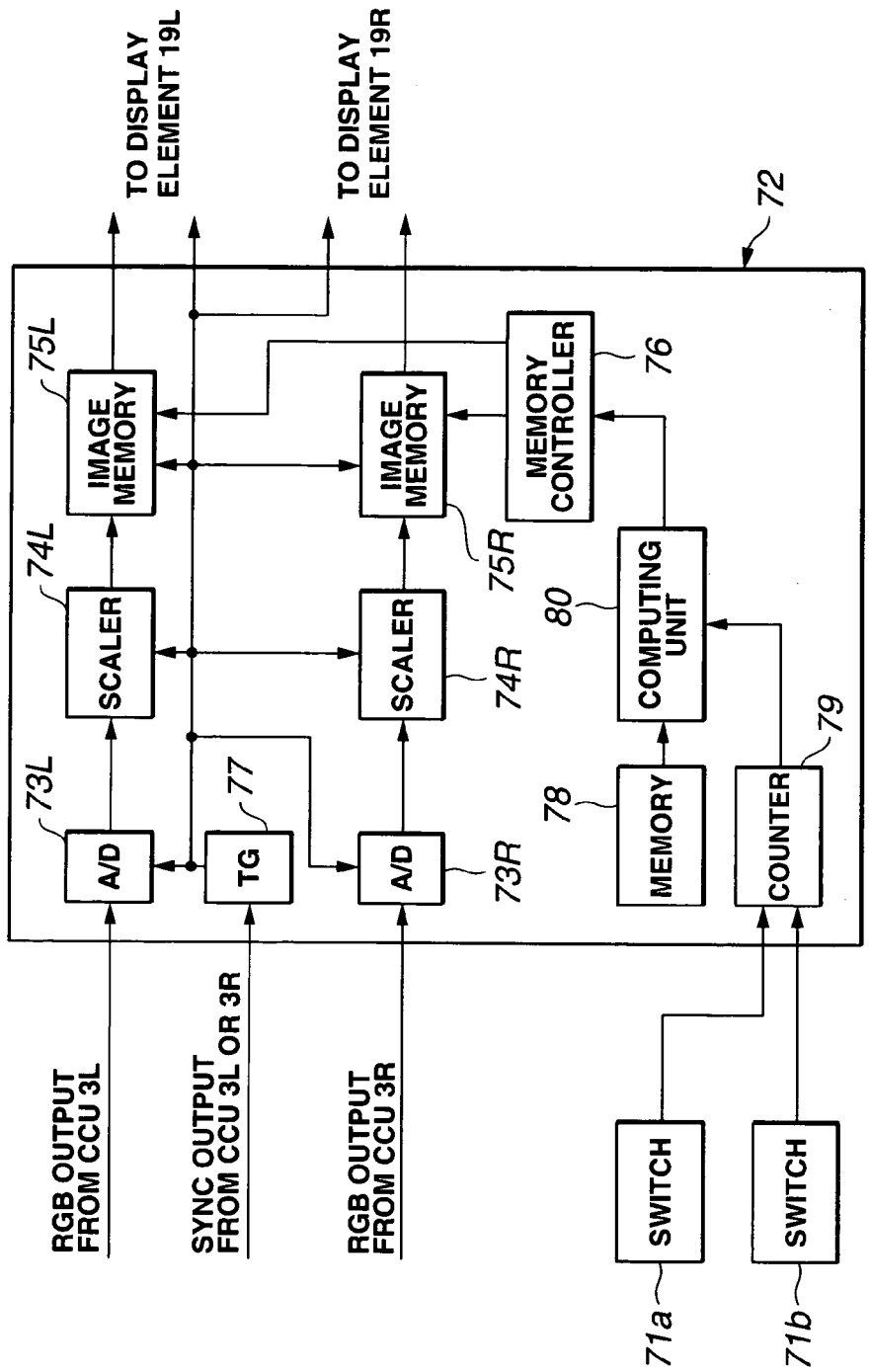

FIG. 15 shows the structure of the display control unit 72. The display control unit 72 includes the switches 71a and 71b, AD circuits 73L and 73R for converting analog video signals output from the CCUs 3L and 3R into digital signals, and scaler circuits 74L and 74R, which receive outputs of the AD circuits 73L and 73R, for converting the format of images by processing, e.g., pixel interpolation, to match the format of the display elements 19L and 19R.

The display control unit 72 further includes image memories 75L and 75R for storing each of outputs of the scaler circuits 74L and 74R as image data of one frame, a memory controller 76 for controlling the respective operations of the image memories 75L and 75R, and a TG 77 for generating operation clocks for the AD circuits 73L and 73R, the scaler circuits 74L and 74R, and the image memories 75L and 75R on the basis of a common sync signal output from the CCU 3L or 3R.

In addition, the display control unit 72 includes a memory 78 which previously stores the width of, e.g., a black signal serving as a mask signal to be output when the switch 71a or 71b is pressed once, a counter circuit 79 for counting the number of operating times of each of the switches 71a and 71b, and a computing unit 80 which, upon receiving a count value from the counter circuit 79, reads the corresponding information from the memory 78 and outputs the information to the memory controller 76.

According to the present embodiment, assuming that the CCUs 3L and 3R output common CCD drive signals to the CCDs 16L and 16R, respectively, the display control unit 72 has the structure shown in FIG. 15. When a common CCD drive signal is not used, two TGs 77L and 77R may be used instead of the TG 77 in FIG. 15.

In addition, the maximum number of times N to prevent images from being excessively shielded when the objective lenses 9L and 9R are too close to the object and the maximum number of times F to prevent images from being excessively shielded when the objective lenses 9L and 9R are too far from the object are recorded (stored) in the memory 78.

When the switch 71a is pressed, the memory controller 76 controls the image memories 75L and 75R so that black signals with a predetermined width are displayed from the outer portions of the display elements 19L and 19R, respectively. When the switch 71b is pressed, the memory controller 76 controls the image memories 75L and 75R so that black signals with a predetermined width are displayed from the inner portions of the display elements 19L and 19R, respectively. The counter circuit 79 includes, e.g., two counter segments (first and second counter segments).

While the black signals are displayed in the respective outer portions, when the switch 71b is pressed, each outer black signal is reduced by the predetermined width. After the outer black signals disappear, black signals are displayed from the inner portions. While the black signals are displayed from the respective inner portions, when the switch 71a is pressed, each inner black signal is reduced by the predetermined width. After the back signals disappear, black signals are displayed in the outer portions.

FIGS. 16A and 16B indicate shielding (masking) examples in display screens on the display elements 19L and 19R using black signals when the switch 71a is pressed and when the switch 71b is pressed.

FIG. 16A shows a case where the switch 71a is operated twice in non-masking mode. In this case, two masking signals each having a predetermined width are displayed in the outer portion on the display screen of each of the display elements 19L and 19R. In other words, the outer portion of each image is shielded.

When the switch 71b is pressed three times in the state in FIG. 16A, a state shown in FIG. 16B is obtained. When the switch 71b is pressed once in the non-masking mode instead of in the state of FIG. 16A, the state in FIG. 16B is obtained. In this case, one masking signal with a predetermined width is shown in the inner portion on the display screen of each of the display elements 19L and 19R. In other words, the inner portion of each image is shielded.

When a value of the memory 78 is changed, the width of black to be output when the switch 71a or 71b is pressed can be changed. Alternatively, the width of black can be increased by continuously pressing the switch. Outputs of the image memories 75L and 75R and the TG 77 are output to the display elements 19L and 19R, respectively.

Figure 17:
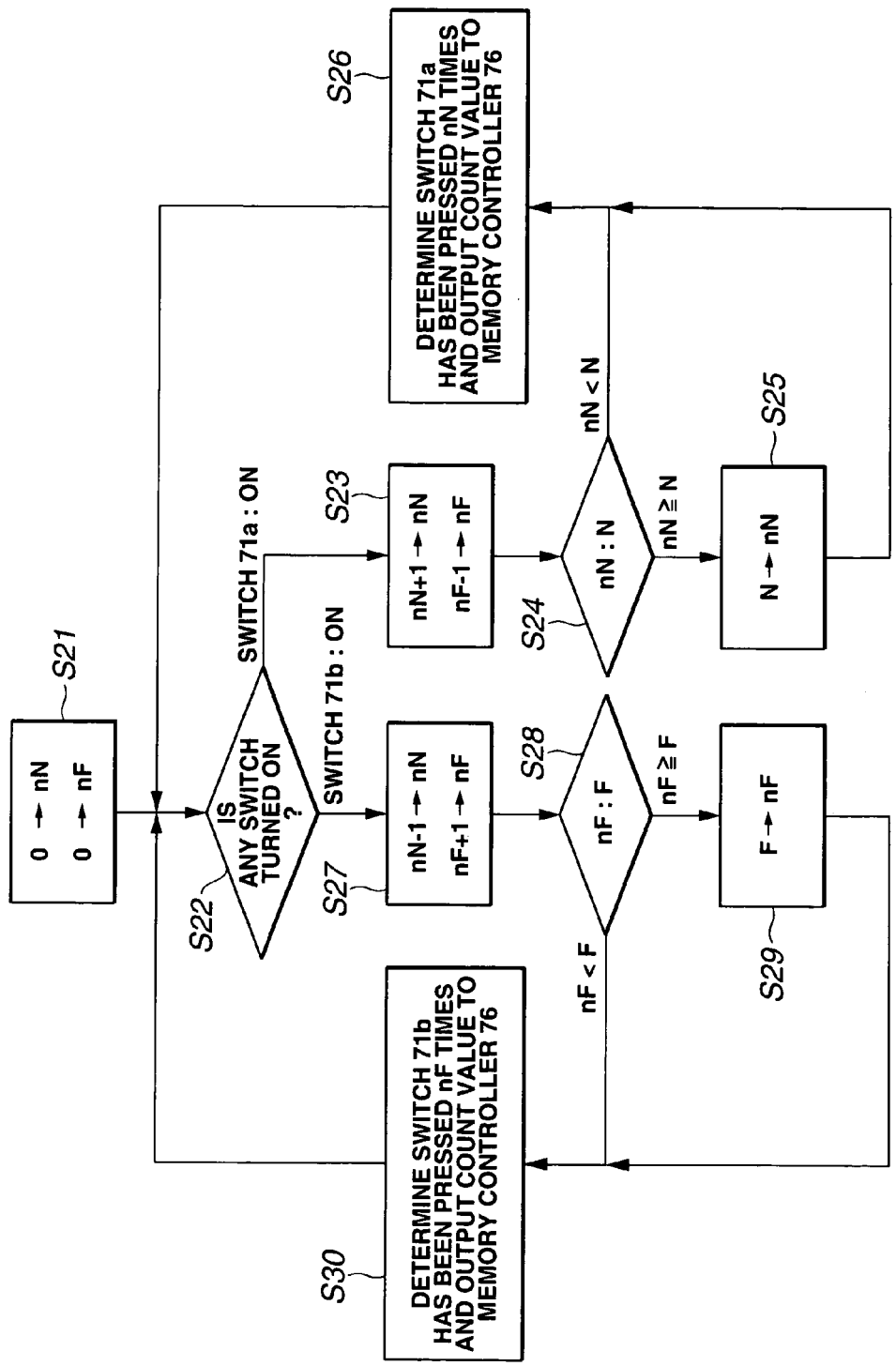

FIG. 17 shows a flowchart of the operation of the computing unit 80.

In step S21, a count value nN of the first counter segment for counting the number of operating times of the switch 71a and a count value nF of the second counter segment for counting the number of operating times of the switch 71b are reset to 0 in the counter circuit 79. In FIG. 17, the reset operation is simply described such that zero is substituted into each of the count values nN and nF.

In step S22, the computing unit 80 determines whether any switch is turned on. In other words, whether the counter circuit 79 outputs two count outputs is determined. As a result of the determination, if the switch 71a is turned on, as shown in step S23, the count value nN of the first counter segment is incremented by one and the count value nF of the second counter segment is decremented by one.

After that, in step S24, the count value nN of the first counter segment is compared to the predetermined number of switching times N, at which it is determined based on, e.g., measurement that stereoscopic vision is not provided if the objective lenses 9L and 9R are closer to the object.

As a result of the comparison, e.g., when $nN \geqq N$, as shown in step S25, the count value nN of the first counter segment is set to this number of switching times N. As shown in step S26, the computing unit 80 determines that the switch 71a has been pressed the number of times corresponding to the count value nN (=N) of the first counter segment and outputs the count value indicating the number of times to the memory controller 76. Then, the operation is returned to step S22.

On the other hand, when it is determined in step S24 that nN<N, as shown in step S26, the computing unit 80 determines that the switch 71a has been pressed the number of times corresponding to the count value nN of the first counter segment and outputs the count value indicating the number of times to the memory controller 76. Then, the operation is returned to step S22.

When it is determined in step S22 that the switch 71b is turned on, as shown in step S27, the count value nN of the first counter segment is decremented by one and the count value nF of the second counter segment is incremented by one. After that, in step S28, the count value nF of the second counter segment is compared to the predetermined number of switching times F, at which it is determined based on, e.g., measurement that stereoscopic vision is not provided if the objective lenses 9L and 9R are farther from the object.

As a result of the comparison, e.g., when $nF \geqq F$, as shown in step S29, the count value nF of the second counter segment is set to the number of switching times F. As shown in step S30, the computing unit 80 determines that the switch 71b has been pressed the number of times corresponding to the count value nF (=F) of the second counter segment and outputs the count value indicating the number of times to the memory controller 76. Then, the operation is returned to step S22.

On the other hand, when it is determined in step S28 that nf<F, as shown in step S30, the computing unit 80 determines that the switch 71b has been pressed the number of times corresponding to the count value nF of the second counter segment and outputs the count value indicating the number of times to the memory controller 76. Then, the operation is returned to step S22.

According to the present embodiment, since the stereoscopic endoscope 2 does not need position detecting means, the size of the stereoscopic endoscope 2 can be reduced. In addition, a complex mechanism operatively associated with the focusing unit 5C can be omitted, so that the stereoscopic endoscope system 1C can be easily realized.

Image pickup areas, which are not picked up in common by both image pickup means as described in the first embodiment, can be easily masked by operating the switches. Thus, endoscopic images which allow an operator to easily view stereoscopically or to easily create perception of depth can be provided to the operator. Since images which easily permit stereoscopic viewing can be provided to the operator, the operator can easily and smoothly carry out surgery.

The present embodiment has been described with respect to the case where images, based on left and right video signals of the CCUs 3L and 3R, to be displayed on the display elements 19L and 19R are electrically masked from the outer or inner portions interlockingly. The present embodiment can also be applied to the case where images are mechanically masked as in the second embodiment.

For example, the switches 71a and 71b are arranged in the shielding plate control unit 62. When the switch 71a is operated, the motor 63 with the pulley is rotated counterclockwise such that the display screens on the display elements 19L and 19R are respectively masked from the outer portions as shown in FIG. 13C. When the switch 71b is operated, the motor 63 with the pulley is rotated clockwise such that the display screens on the display elements 19L and 19R are respectively masked from the inner portions as shown in FIG. 13A.

According to the above-mentioned embodiments, each stereoscopic endoscope 2 includes image pickup means for picking up left and right optical images. The present invention is not limited to the structure. For example, the present invention can be applied to, e.g., an optical stereoscopic endoscope in which left and right optical images can be observed as stereoscopic vision through respective eyepiece sections, and an external camera mounted stereoscopic endoscope constructed such that a television camera or a camera head including image pickup means for picking up left and right optical images is attached to eyepiece sections of the optical stereoscopic endoscope.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A stereoscopic-endoscope display control apparatus comprising:
    a stereoscopic endoscope including:
        left and right optical systems having a left and right parallax,
        left and right image forming optical systems respectively arranged on left and right optical axes along respective optical axes of the left and right optical systems, each of the left and right image forming optical systems forming an image of a same subject, and
        left and right image pickup devices arranged at respective image forming positions of the left and right image forming optical systems;
    left and right focusing optical systems for adjusting focal distance according to a distance from the left and right optical systems to the subject by being moved in conjunction with each other in the left and right optical axes directions, respectively, to focus and form respective images on the left and right image pickup devices; and
    a masking device for masking left and right video signals using electric masking signals on the basis of the focal distance information, the left and right video signals being generated from the left and right image pickup signals at a timing corresponding to the image pickup areas that are not picked up in common by both the left and right image pickup devices, wherein
    the left and right image pickup devices are fixed irrespective of movement of the left and right focusing optical systems, and the left and right areas masked by the masking device correspond to essentially symmetrical areas with respect to the left and right image pickup devices.

2. The stereoscopic-endoscope display control apparatus according to claim 1, wherein the masking device is capable of masking the image pickup areas that are not picked up in common by both the left and right image pickup devices in accordance with an operation instructed by a masking-instruction operating device.

3. The stereoscopic-endoscope display control apparatus according to claim 1, wherein the masking device includes a timing generator for determining the timing, corresponding to left and right picked up areas not picked up in common by both the left and right image pickup devices, by counting clocks synchronously with adjacent two horizontal synchronization signals for a video signal display period between the horizontal synchronization signals in order to mask the left and right video signals using the electric masking signals.

4. A stereoscopic endoscope system comprising:
    a stereoscopic endoscope having:
        left and right optical systems having a left and right parallax,
        left and right image forming optical systems respectively arranged on left and right optical axes along respective optical axes of the left and right optical systems, each of the left and right image forming optical systems forming an image of a same subject, and
        left and right image pickup devices arranged at respective image forming positions of the left and right image forming optical systems;
    left and right focusing optical systems for adjusting focal distance according to a distance from the left and right optical systems to the subject by being moved in conjunction with each other in the left and right optical axes directions, respectively, to focus and form respective images on the left and right image pickup devices;
    a video signal generating device for generating left and right video signals from left and right image pickup signals obtained by the left and right image pickup devices;
    a display device for displaying the left and right video signals; and
    a masking device for masking parts of the left and right video signals or images displayed in the display device, the masking device including an electrical masking device for partially and electrically masking the parts of the left and right video signals corresponding to left and right areas not picked up in common by both the left and right image pickup devices based on focal distance information, wherein
    the left and right image pickup devices are fixed irrespective of movement of the left and right focusing optical systems, and the left and right areas masked by the masking device correspond to essentially symmetrical areas with respect to the left and right image pickup devices.

5. The stereoscopic endoscope system according to claim 4, further comprising a mechanism for moving the left and right focusing optical systems in conjunction with each other in the left and right optical axes directions.

6. The stereoscopic endo scope system according to claim 5, wherein the mechanism for moving the focusing optical systems moves left and right movable optical systems along the left and right optical axes, the left and right movable optical systems at least partially including the left and right image forming optical systems provided in the stereoscopic endoscope.

7. The stereoscopic endoscope system according to claim 5, wherein the electrical masking device uses information regarding the focal distance of the left and right image pickup devices moved by the mechanism moving the focusing optical systems to partially and electrically mask the left and right video signals corresponding to the image pickup areas that are not picked up in common by both the left and right image pickup devices at the focal distance.

8. The stereoscopic endoscope system according to claim 4, wherein when the focusing optical systems change the focal distance of the left and right image pickup devices toward a far point or a near point, the masking device partially masks the left and right video signals corresponding to the image pickup areas that are not picked up in common by both the left and right image pickup devices in accordance with the change.

9. The stereoscopic endoscope system according to claim 4, wherein the masking device includes an instruction operating device for performing an instruction operation for masking, and a masking signal generating device for generating masking signals to partially mask left and right video signals in accordance with the instruction operation by the instruction operating device such that the outer or inner portions of display screens are masked, when the left and right video signals are respectively output to two display elements constituting the display device.

10. A stereoscopic endoscope system comprising:
    a stereoscopic endoscope including:
        left and right optical systems having a left and right parallax,
        left and right image forming optical systems respectively arranged on left and right optical axes along respective optical axes of the left and right optical systems, each of the left and right image forming optical systems forming an image of a same subject, and
        left and right image pickup devices arranged at respective image forming positions of the left and right image forming optical systems;
    left and right focusing optical systems for adjusting focal distance according to a distance from the left and right optical systems to the subject by being moved in conjunction with each other in the left and right optical axes directions, respectively, to focus and form respective images on the left and right image pickup devices;
    a distance detecting device for detecting information regarding the distance to the object on the basis of the focal distance set by the focusing optical systems;
    a video signal generating device for generating left and right video signals from left and right image pickup signals obtained by the left and right image pickup devices; and
    a masking device for masking left and right image pickup areas that are not picked up in common by both the left and right image pickup devices or display areas corresponding to the left and right image pickup areas being not picked up in common on the basis of the focal distance information, wherein
    the left and right image pickup devices are fixed irrespective of movement of the left and right focusing optical systems, and the left and right pickup areas masked by the masking device correspond to essentially symmetrical areas with respect to the left and right image pickup devices.

11. The stereoscopic endoscope system according to claim 10, wherein the masking device includes an electrical masking device for electrically masking images in the display areas corresponding to the image pickup areas that are not picked up in common by both the left and right image pickup devices.

12. The stereoscopic endoscope system according to claim 11, wherein the electrical masking device includes a masking signal generating device for generating masking signals to electrically mask left and right video signals corresponding to the image pickup areas that are not picked up in common by both the left and right image pickup devices.

13. The stereoscopic endoscope system according to claim 10, wherein the masking device includes a mechanical masking device for mechanically masking the display areas corresponding to the image pickup areas that are not picked up in common by both the left and right image pickup devices.

14. The stereoscopic endoscope system according to claim 13, wherein the mechanical masking device moves shielding plates to mechanically mask the display areas.

15. The stereoscopic endoscope system according to claim 10, wherein the masking device includes a masking range calculating device for calculating the image pickup areas that are not picked up in common by both the left and right image pickup devices at the focal distance or display areas corresponding to the image pickup areas being not picked up in common on the basis of the distance information obtained by the distance detecting device.

16. The stereoscopic endoscope system according to claim 15, wherein the masking device masks the image pickup areas that are not picked up in common by both the left and right image pickup devices or the display areas corresponding to the image pickup areas being not picked up in common calculated by the masking range calculating device.

* * * * *